(12) United States Patent
Kaloudis et al.

(10) Patent No.: US 11,605,047 B2
(45) Date of Patent: Mar. 14, 2023

(54) PREDICTIVE POST-HARVEST STORED COMMODITY MANAGEMENT METHODS

(71) Applicant: CENTAUR ANALYTICS, INC., Ventura, CA (US)

(72) Inventors: Efstathios Kaloudis, Athens (GR); Sotirios Bantas, Volos (GR); Apostolos Lerios, Austin, TX (US)

(73) Assignee: CENTAUR ANALYTICS, INC., Ventura, CA (US)

( * ) Notice: Subject to any disclaimer, the term of this patent is extended or adjusted under 35 U.S.C. 154(b) by 0 days.

(21) Appl. No.: 17/309,054

(22) PCT Filed: Oct. 31, 2019

(86) PCT No.: PCT/US2019/059212
§ 371 (c)(1),
(2) Date: Apr. 16, 2021

(87) PCT Pub. No.: WO2020/092804
PCT Pub. Date: May 7, 2020

(65) Prior Publication Data
US 2021/0365879 A1 Nov. 25, 2021

Related U.S. Application Data

(60) Provisional application No. 62/754,404, filed on Nov. 1, 2018.

(51) Int. Cl.
*G06Q 10/08* (2012.01)
*G06F 30/28* (2020.01)
(Continued)

(52) U.S. Cl.
CPC .......... *G06Q 10/0832* (2013.01); *A01G 7/02* (2013.01); *A01N 63/00* (2013.01);
(Continued)

(58) Field of Classification Search
CPC ........ A01N 63/00; A01N 63/10; A01N 63/12; A01N 63/14; A01N 63/16; A01N 63/20;
(Continued)

(56) References Cited

U.S. PATENT DOCUMENTS

| 9,087,312 | B1 | 7/2015 | Mewes et al. | |
|---|---|---|---|---|
| 2010/0257125 | A1* | 10/2010 | Kallestad | A01F 25/22 705/418 |

(Continued)

FOREIGN PATENT DOCUMENTS

| CN | 107544342 A | 1/2018 |
|---|---|---|
| CN | 106094614 B | 10/2018 |
| WO | 2014/039913 A1 | 3/2014 |

OTHER PUBLICATIONS

Yongfu Xu, et al, "Simulating the bulk storage of foodstuffs," Journal of Food Engineering 39, pp. 23-29 (1999) (Year: 1999).*

(Continued)

*Primary Examiner* — Steven W Crabb
(74) *Attorney, Agent, or Firm* — Ascenda Law Group, PC

(57) ABSTRACT

Systems and methods for managing post-harvest crop quality and pests. A post-harvest monitoring system receives sensor device measurements from sensors deployed within a commodity storage facility. The system analyzes the sensor measurements and, optionally, other data, and provides a user with a representation of the storage facility that includes air flow, temperature, and/or moisture content readouts, along with stored commodity quality and/or stored commodity business metrics predictions concerning infestation level, visible mold, dry matter loss, germination capacity, gas concentration, and estimates of commodity value and profit margin under a variety of post-harvest monitoring system-recommended or user-specified scenarios. Use of the system thus enhances stored commodity quality, marketabil- (Continued)

ity and food safety by providing solutions that combat spoilage manifestations and guide end users to efficient pest management.

17 Claims, 16 Drawing Sheets

(51) Int. Cl.
| | |
|---|---|
| *A01G 7/02* | (2006.01) |
| *A01N 63/00* | (2020.01) |
| *G01N 33/00* | (2006.01) |
| *G06Q 50/02* | (2012.01) |
| *G06F 111/10* | (2020.01) |
| *G06F 17/13* | (2006.01) |
| *G06Q 10/0832* | (2023.01) |

(52) U.S. Cl.
CPC ......... *G01N 33/0075* (2013.01); *G06F 30/28* (2020.01); *G06Q 50/02* (2013.01); *G06F 17/13* (2013.01); *G06F 2111/10* (2020.01)

(58) Field of Classification Search
CPC ........ A01N 63/22; A01N 63/23; A01N 63/25; A01N 63/27; A01N 63/28; A01N 63/30; A01N 63/32; A01N 63/34; A01N 63/36; A01N 63/38; A01N 63/40; A01N 63/50; A01N 63/60; A01N 65/03; G06Q 10/0832; G06Q 50/02; G06Q 10/08; A01G 7/02; G01N 33/0075; G06F 30/28; G06F 30/20
See application file for complete search history.

(56) References Cited

U.S. PATENT DOCUMENTS

| | | |
|---|---|---|
| 2015/0106434 A1 | 4/2015 | Fiene et al. |
| 2018/0120225 A1 | 5/2018 | Ditterich |
| 2018/0144293 A1 | 5/2018 | Christie et al. |
| 2018/0320967 A1 | 11/2018 | Kaloudis et al. |
| 2019/0262082 A1* | 8/2019 | Krimsky ................ A61B 1/051 |
| 2019/0265082 A1* | 8/2019 | Zafar ..................... G01K 1/024 |

OTHER PUBLICATIONS

Gbenga Olantunde et al., "CFD modeling of air flow distribution in rice bin storage system with different grain mass configurations," Biosystems Engineering 151 pp. 286-297 (2016) (Year: 2016).*
Kaleta and K. Gornicki, "Criteria of Determination of Safe Grain Storage Time—A Review", 2013, pp. 295-318 (Year: 2013).*
M.A. van Sommeren, "Modelling and simulation of rot in potato storage facilities," BSc Thesis Biosystems Engineering pp. 1-75 (2016) (Year: 2016).*
Barreto; et al., "Analysis of storage conditions of a wheat silo-bag for different weather conditions by computer simulation", Biosystems Engineering (2013), 116:497-508.
Driscoll; et al., "Prediction of insect populations in grain storage", Journal of Stored Products Research (2000), 36(2):131-151.
Emekci; et al., "Respiration of stored product pests in hermetic conditions", Proceedings of the International Conference on Controlled Atmosphere and Fumigation in Stored Product, Fresno, CA, Oct. 29-Nov. 3, 2000, pp. 26-35.
Lawrence; et al., "Three-Dimensional Transient Heat, Mass, Momentum, and Species Transfer in the Stored Grain Ecosystem: Part I., Model Development and Evaluation", Transactions of the ASABE (2013), 56(1):179-188.
Navarro and Noyes, editors, "The Mechanics and Physics of Modern Grain Aeration Management", CRC Press (2002), London, 674 pgs.
Thompson, "Temporary Storage of High-Moisture Shelled Corn Using Continuous Aeration", Transactions of the ASAE (1972), 15(2):333-337.
International Preliminary Report on Patentability dated May 14, 2021, from The International Bureau of WIPO, for International Patent App. No. PCT/US2019/059212 (filed Oct. 31, 2019), 8 pgs.
International Search Report and Written Opinion dated Jan. 17, 2020, from the ISA/US, for International Patent Application No. PCT/US19/59212 (filed Oct. 31, 2019), 13 pgs.

* cited by examiner

PREDICTIVE POST-HARVEST STORED COMMODITY MANAGEMENT METHODS

RELATED APPLICATIONS

This application claims priority to U.S. Provisional Application No. 62/754,404, filed Nov. 1, 2018.

FIELD OF THE INVENTION

The present invention relates generally to post-harvest crop management, and more particularly to methods and systems for managing crop quality and pests, e.g., using agricultural sensors, data analytics, crop storage, and pest management techniques.

BACKGROUND

End users such as farmers, operators of storage and logistics facilities, agronomists, food scientists, pest control technicians and quality control experts, have used certain methods in the prior art to combat post-harvest losses, waste, and their root causes including pest infestations. These methods have employed technology which is currently outdated to perform functions such as spoilage detection, fumigation chemical (i.e., fumigant) dosage monitoring, and insect infestation detection. These legacy methods have only partially addressed the problem of post-harvest waste. Moreover, prior methods for post-harvest monitoring and quality control have been cumbersome or impractical, requiring a high degree of manual operator involvement, error-prone, and therefore difficult to deploy at large scale. Primary shortcomings of these methods include: (1) the difficulty of installing or retrofitting a storage facility with monitoring systems (such as thermocouples); (2) the poor long-term durability and reliability of these systems; and (3) the fact that the previous monitoring methods have only been able to detect aggravated cases of spoilage, by which time corrective action and remediation are no longer possible.

BRIEF DESCRIPTION OF THE DRAWINGS

The present invention is illustrated by way of example, and not limitation, in the figures of the accompanying drawings, in which.

DETAILED DESCRIPTION

Figure 1:
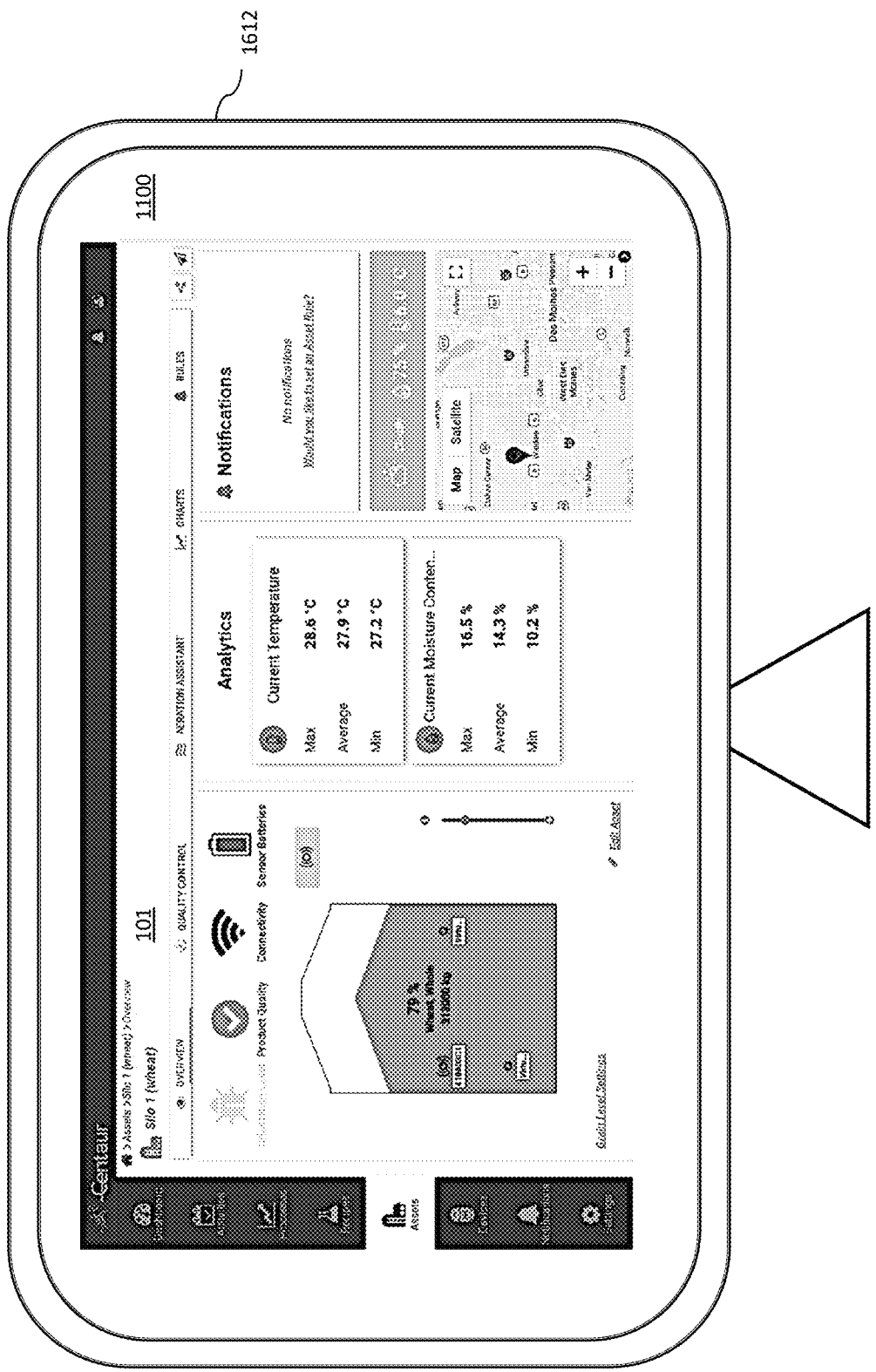
FIG. 1 depicts an exemplary user interface for a post-harvest monitoring system for monitoring and managing stored commodity quality in accordance with some embodiments of the invention.

Recognizing the shortcomings of prior methods for post-harvest monitoring and quality control, the present inventors have determined there is a need for systems and approaches that solve these problems, for example, by improving prediction accuracies of locations and amounts of spoilage (such as dry matter loss, mold, and germination loss) through thermodynamic simulations within the stored commodity and under the effects of weather and microclimate at the storage location, as well as for leveraging such predictions to automatically control ventilation or aeration of the stored commodity. The present invention addresses aspects of this need, hence, embodiments of apparatuses, computer systems, computer readable media, and methods for post-harvest crop integrity and pest management are described, aiming to enhance quality, marketability and food safety. For example, embodiments of the invention described herein provide solutions that effectively combat spoilage manifestations, such as mycotoxins and insects, and guide end users to efficient pest management in post-harvest storage of agricultural commodities. The solutions may be based on cloud-connected wireless sensors (edge devices), real-time data monitoring, data analytics and computational fluid dynamics simulations.

Computational fluid dynamics (CFD) approaches are described herein. These analytical approaches include, for example, using a three-dimensional CFD model incorporating a finite volume approach for discretizing constituent equations, incorporating an air flow component using the Navier-Stokes equation, an oxygen concentration component, a dry matter loss component, a visible mold component, and a germination loss component. Also included are approaches in which analytical models incorporate exterior or ambient weather forecasts, and approaches which enable automated preventative or corrective aeration of a stored commodity in order to minimize spoilage and extend the safe storage time for the stored commodity. Finally, disclosed approaches enable predicting granular fumigation treatment durations and recommended dosages for crop storage areas for which no prior historical data is available.

This invention may further incorporate unsupervised learning techniques to improve upon the initial, generic analytical models and their system default or user-provided parameters through the use of actual measurements, whether those were taken prior to the installation of sensors contemplated by this invention, or by the sensors of this invention, and whether at the same storage facility where the model is in use or at other storage facilities that are deemed to be sufficiently similar. For example, correlating real-time insect population data to fumigant levels may help tailor initial, generic estimates of lethal fumigant levels to the specific levels suitable for the pest population at the storage facility, or other nearby facilities. Additionally, CFD simulations can be combined with sensor data to automatically (e.g., via machine learning methods) adjust certain correction factors or other parameters used in a CFD simulation so that the simulation results match actual data streams; then, the "trained" CFD simulation makes more accurate predictions. Such approaches may be applied to both predictive pest management and crop spoilage detection use cases.

As used herein, the terms "commodity," "crop," and "product" mean a harvested agricultural product, such as harvested crops, that may include, for example, grains, oilseeds, fruits, vegetables, fiber crops (e.g., cotton, hemp, sisal), wood (e.g., lumber, sawdust), tobacco, or coffee. Notably, a commodity, crop, or product may be an agricultural product as it stood immediately after harvesting, or as it stood after partial processing (e.g., after removal of some foreign matter) or full processing (e.g., after drying or grounding).

As used herein, the term "storage facility" means a storage location for a commodity, such as a silo, warehouse, or shipping container. Notably, a facility may be as simple as a covered or uncovered, indoor or outdoor, aggregated quantity of the commodity (e.g., a pile), with or without containment by a man-made structure (e.g., a silo), natural structure (e.g., a dugout or pit), or some elementary protective equipment (e.g., a bag or crate). Moreover, storage need be neither stationary (e.g., it may be a shipping container during shipment) nor last for any specific duration (i.e., it may last hours or years, sometimes depending upon the sensitivity of the commodity to spoilage).

Stored Product Quality: Spoilage Protection

The process of crop storage often involves microbiological contamination and infestation. The composition of these microbial contaminants is of great importance, since at high moisture levels these microorganisms could grow and alter the properties of the product. Product deterioration can also occur due to respiration of the product itself and of the accompanying microorganisms.

Figure 2:
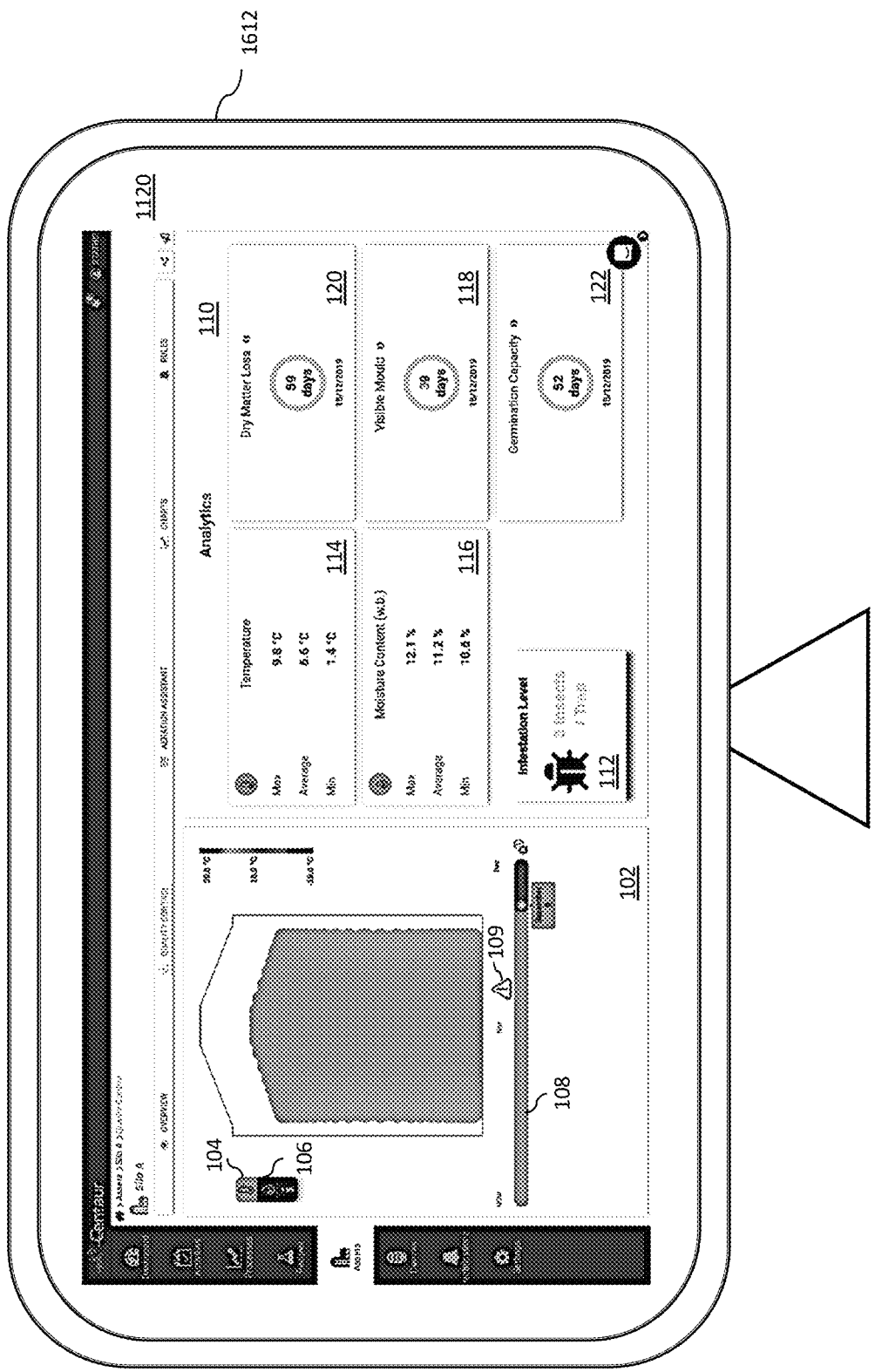
FIG. 2 depicts an exemplary user interface for a post-harvest monitoring system for monitoring and managing stored commodity quality in accordance with some embodiments of the invention.
Figure 3:
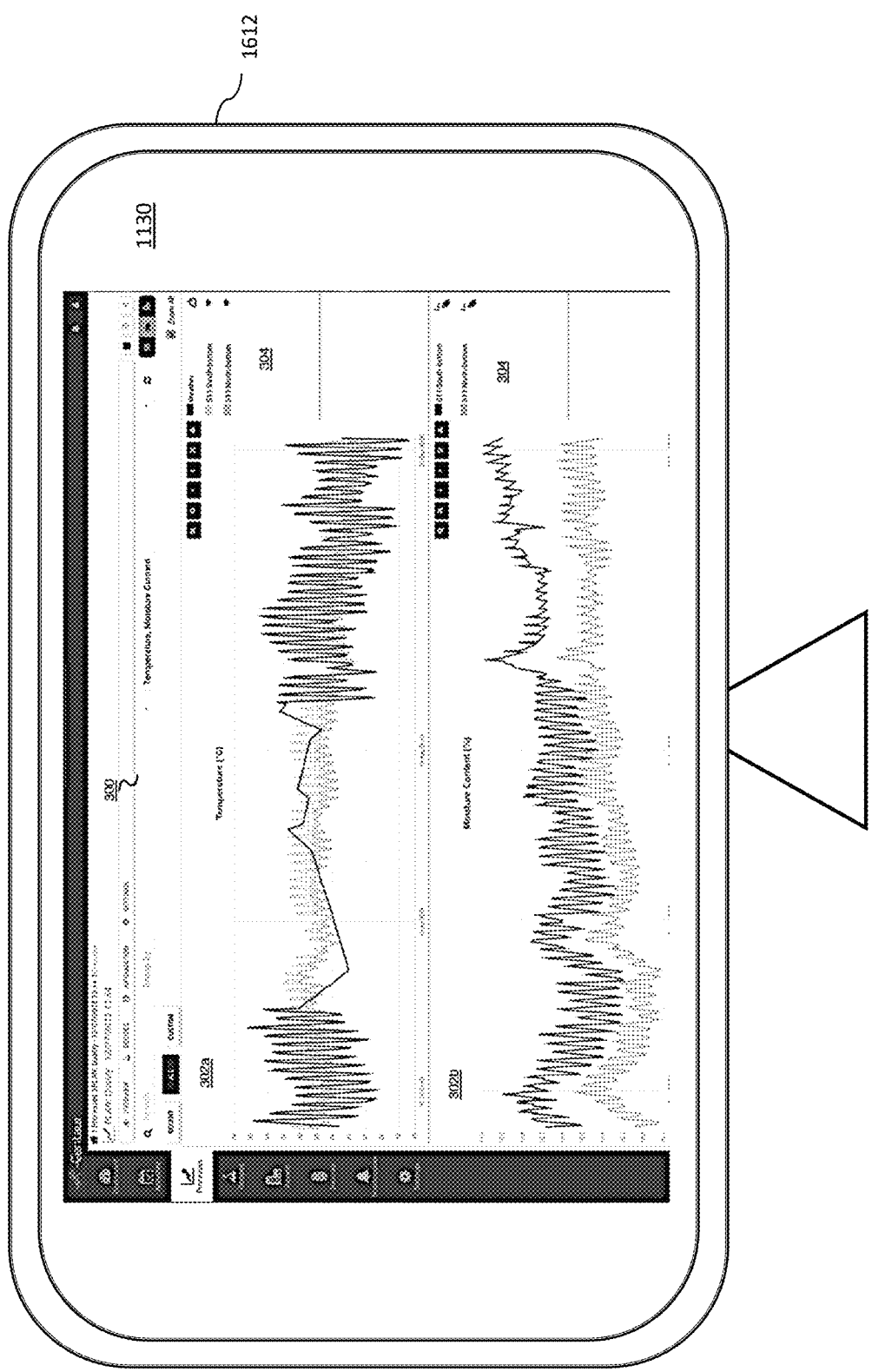
FIG. 3 depicts an exemplary user interface for a post-harvest monitoring system for monitoring and managing stored commodity quality in accordance with some embodiments of the invention.

FIGS. 1-3 show exemplary user interfaces 1100, 1120, and 1130 for a post-harvest monitoring system for monitoring and managing stored commodity quality, e.g. for display at a user device such as a personal computer or smart phone.

User interface 1100 of FIG. 1 includes a navigation panel 101 for toggling between various user interfaces concerning a specific storage facility for a commodity (in the example of FIG. 1, labeled "Silo 1 (wheat)"). Navigation panel 101 may be used to select user interfaces for overview, quality control, aeration assistant, charts, and rules concerning the storage facility. User interface 1100 presents an overview of the storage facility. It includes a storage facility representation showing the type of stored commodity, its mass (which may be a user input or calculated automatically by an installed fill level sensor) and the installed locations of sensors. Icons above the storage facility present brief information on infestation levels, product quality, sensor connectivity, and sensor battery levels. User interface 1100 provides information on the current temperature and moisture content of the commodity, a geographical map of the storage facility location, the current weather conditions at the same location and notifications pertaining to the facility's operation.

User interface 1120 of FIG. 2 illustrates quality control for the storage facility. It includes a storage facility representation 102 showing current or predicted temperature or moisture levels within the storage facility. A user may select whether temperature or moisture is depicted in the storage facility representation 102 by selecting temperature selector 104 or moisture selector 106; in FIG. 2, the temperature selector 104 is selected. The appearance of storage facility representation 102 is affected by timeline selector 108 which displays a timeline beginning at the current time ("NOW"), extending to the end of the anticipated storage time period or desired predictive analysis period (whichever comes first), depicting notable predicted events, and marking the point in time associated with the information depicted in the storage facility representation 102.

In FIG. 2, selector 108 indicates that the analysis period extends to December, that an alert condition (109) is anticipated to occur in early November and that storage facility representation 102 is showing a prediction of temperature levels dated approximately 2 months into the future; that prediction is based on a CFD simulation or other analysis model executed or applied by the post-harvest monitoring system (e.g., the platform described below with reference to FIG. 15). An alert condition is a predefined circumstance under which the commodity is expected to be damaged or at risk of being damaged (e.g., spoiled).

In certain embodiments, storage facility representation 102 relies on data derived from current sensor device measurements within the associated storage facility, or from external weather services, to depict the current state of storage facility representation 102. These measurements and/or other external data are inputs (e.g., as time-course data streams) to the post-harvest monitoring system. In certain embodiments, storage facility representation 102 presents air flow, temperature, or moisture content and other quality or business metrics predictions such as infestation level, visible mold, dry matter loss, germination capacity, gas concentration (e.g., carbon dioxide concentration) as discussed herein (see FIG. 10), and estimates of commodity value and profit margin under a variety of system-recommended or user-specified scenarios regarding potential remediation or other management activities (such as an early sale of a portion of the stored commodity). Quality metrics may be directly measured (e.g., using an appropriate sensor device), calculated based on a current direct measurement of a related physical descriptor (e.g., calculating the current moisture level of a commodity based on a relative humidity measurement of the surrounding air), or predicted for a future time point (e.g., using a CFD simulation). Business metrics may be computed using current or predicted quality metrics, operational cost information (e.g., local cost of fumigant or electricity, time-varying or constant), external predictions (e.g., values of futures contracts on commodities), and system-recommended or user-specified scenarios regarding potential remediation or other management activities (in order to enable the user to perform a cost/benefit analysis of potential remediation or other management activities).

Analytics panel 110 provides a user-configurable collection of current status and/or prediction indicators that provide quality or business metrics about the commodity stored in the storage facility. For example, infestation level indicator 112 may show a current or predicted pest infestation level based on a count of insects in a trap located within the storage facility and associated predictions by an analysis model. (The infestation level indicator may be calculated based on more than one trap within the storage facility, e.g., as the mean, median, minimum, or maximum of counts across all traps; also, the count at each trap may be taken automatically, using a sensor in the trap.) Temperature indicator 114 may present current or predicted temperature information relating to the storage facility, such as an exterior, ambient temperature for the storage facility based on an external current or forecasting weather service or based on temperature measured by one or more sensor devices located within the storage facility and associated predictions by an analysis model. (Multiple measurements may be combined into a single indicator, e.g., using the mean, median, minimum or maximum calculations.) Moisture content indicator 116 may present a measured or predicted moisture content based on the measurements of one or more sensor devices located within the storage facility (aggregating multiple measurements e.g., using the mean, median, minimum or maximum calculations) and associated predictions by an analysis model. In certain embodiments, the current or predicted moisture content may be calculated based on an alternative sensor device measurement or prediction, such as relative humidity of the air. Visible mold indicator 118 may present a predicted time period until mold is likely to be apparent on some portion of the commodity within the storage facility. Dry matter loss indicator 120 may present a predicted time period until dry matter loss is likely to be apparent on some portion of the commodity within the storage facility. Germination capacity indicator 122 may present a predicted time period until germination of portions of the commodity is likely to be apparent within the storage facility. In certain embodiments, business metrics indicators may present estimates of the current total value of the commodity within the storage facility, predicted future value if no remediation is undertaken, the cost of recommended remediation or alternative user-selected commodity management scenario, and the predicted future value of the commodity after such actions. In certain embodiments, selecting an indicator accesses additional information or configuration options about the current or predicted measurement shown, such as selecting among the mean, median, maximum, minimum, or other aggregation calculations, or specifying custom commodity management scenarios.

User interface 1130 of FIG. 3 provides the ability to sort and display time-course data (a.k.a. data traces), such as data associated with quality or business metrics and which was obtained by direct measurement in the past, calculated from direct measurement in the past, predicted for the future, or a combination of these, with each data point associated with one point in time. User interface 1130 includes a data set selector 300 which may provide controls for searching for a particular data set in a collection of data sets, for sorting data sets based on a parameter in the data set, or for selecting one or more parameters of the data set to display. User interface 1130 may include one or more data display panels 302a, 302b. In certain embodiments, each data display panel displays one or more time courses of data associated with one quality or business metric (e.g., the temperature quality metric offers one time course for each interior temperature sensor and one for exterior, ambient temperature; the temperature panel may contain any user-selected combination of these time courses). Each data display panel includes a source panel 304 for displaying the source or user-defined label for the data trace, each label corresponding to a single trace or time course within the respective panel. For example, as indicated in source panel 304 of exemplary data display panel 302a, panel 302a shows three data traces, where two traces correspond to sensor devices located within a storage facility for a commodity (e.g., labelled "S11-South-bottom", "S11-North-bottom") and a third trace corresponds to temperature provided by a weather service for the area of the storage facility (e.g., labelled "weather"). In certain embodiments, data traces may be visualized in the same data display panel alongside additional data traces derived from the original data traces via statistical methods (e.g., moving average, best-fit line with or without variance envelopes), user-defined calculations (e.g., the point-by-point difference of two original data traces, or the maximum of any number of original data traces), or a combination of the two (e.g., the difference of two best-fit lines); these derived traces enable the user to perform a visual analysis of the data traces (e.g., to identify trends, remove noise, or compare traces). In certain embodiments, each data trace may be depicted using multiple curves inside the same data display panel, each curve representing one cycle; a cycle is a time period over which a data trace exhibits a reasonably repeatable or predictable pattern of variation (e.g., if a data trace covers a total time span of 9 days, the panel may cover a time period of 24 hours and show three curves, one each for days 1, 5, and 9, so that the user may visualize regular daily cycles and repeatable patterns of intra-day variation, such as temperature rising during daylight hours and dropping through the night; or, if a data trace is associated with fumigant concentration, then a cycle is a treatment and therefore every cycles starts when treatment is initiated, but each cycle may have a different duration, in which case the panel covers the time span of the longest treatment selected for display, and short treatments are visualized as curves that do not extend all the way to the right edge of the panel).

Annotations

Figure 4:
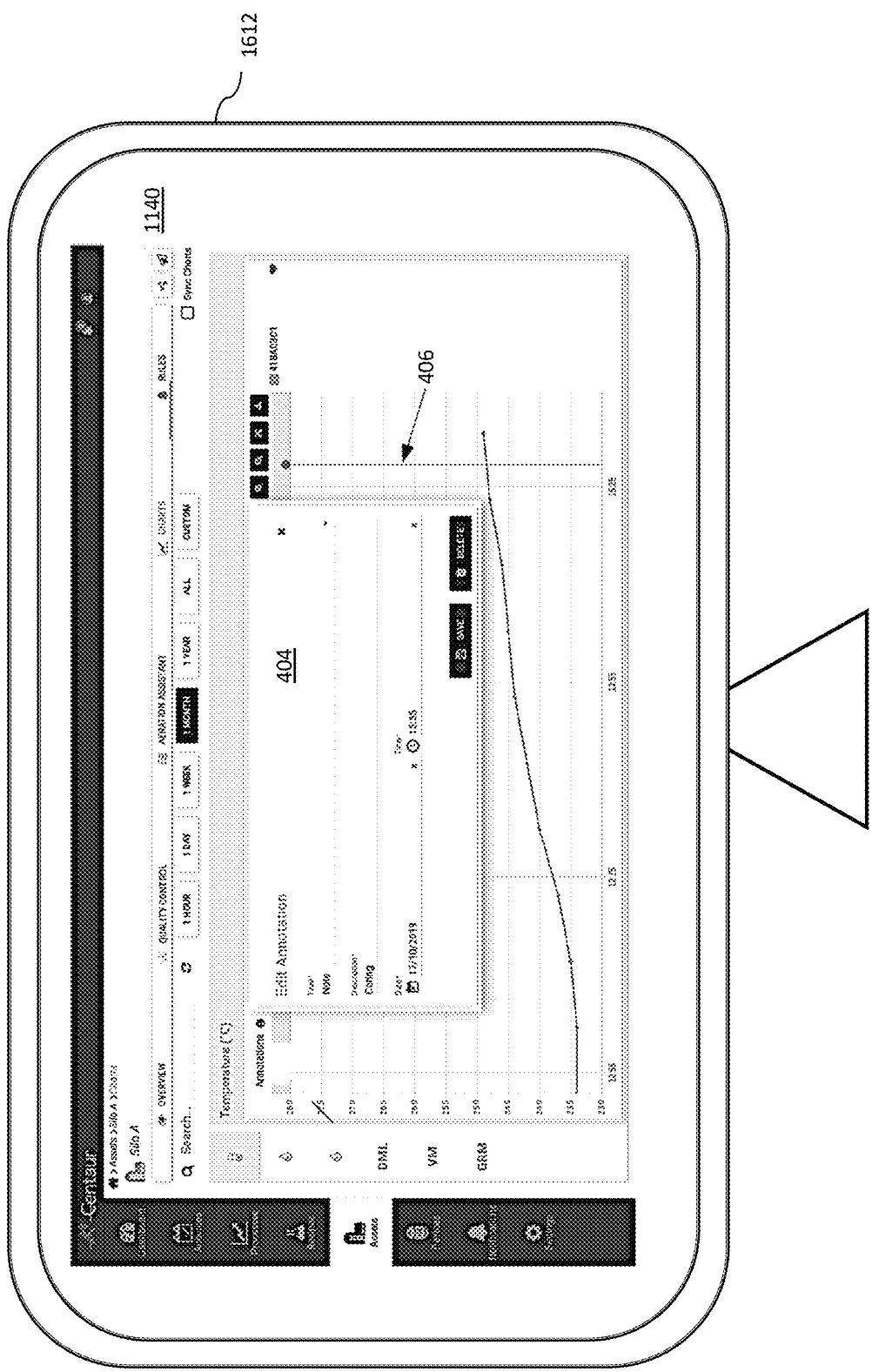
FIG. 4 depicts an exemplary user interface for a post-harvest monitoring system for creating an annotation in accordance with some embodiments of the invention.

User interface 1140 of FIG. 4 provides the ability to create an annotation in a display of time-course data, such as a directly measured, derived from measurements, simulated, or a combination thereof quality or business metric. The user may attach an annotation to a specific point in time in order to mark and describe an event present in the data; the date, time, and description are entered in the corresponding panel 404. Once created, an annotation is visualized as a vertical line 406 in the timeline panel, drawing the user's attention to the event in a user-friendly manner. Using this feature of the invention, storage facility managers can create a detailed calendar log of the stored commodity, associating specific grain conditions with known events thus improving the efficiency of grain management by a team of collaborators.

Rules

Figure 5:
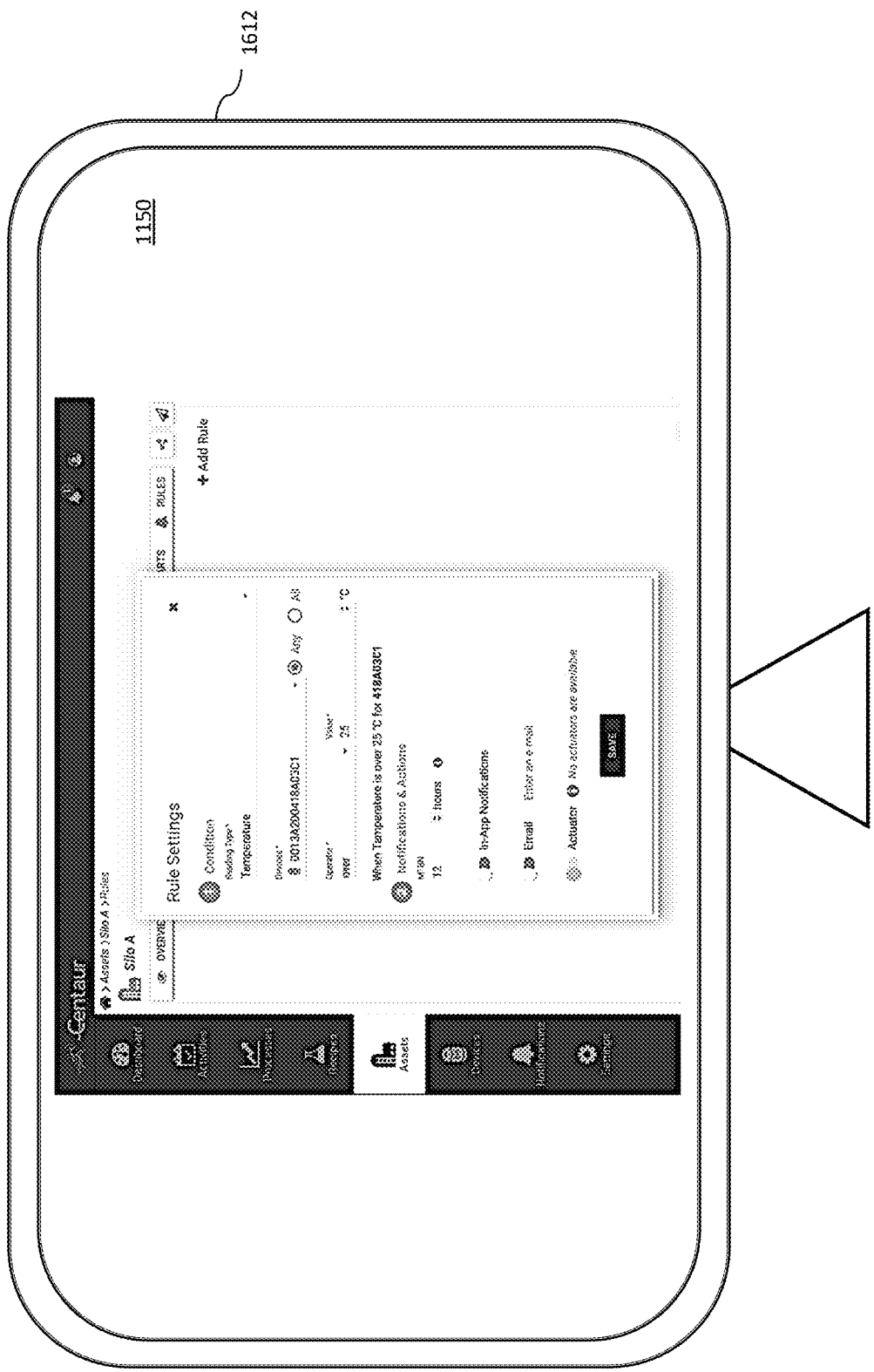
FIG. 5 depicts an exemplary user interface for a post-harvest monitoring system for creating a customizable rule in accordance with some embodiments of the invention.

User interface 1150 of FIG. 5 provides the ability to create rules which trigger based on new values generated for time-course data, such as a directly measured, derived from measurements, simulated, or a combination thereof quality or business metric. The rules apply to a specific storage facility and/or specific commodity and its time-course data. Thus, users receive custom-made alerts (email or in-app) in addition to the default system notifications.

Real-Time Event Detection

Another feature of the invention is detecting or deducing notable events that may occur in a storage facility by constantly analyzing the time-course data. Detection comprises conclusions drawn directly from the data (e.g., newly generated time-course data values crossing a predefined threshold), while deduction comprises conclusions drawn from comparing the current data against a model of its own, or that of similar time-course data in the same or other facilities, past or typical patterns (e.g., temperature time-course data from a malfunctioning sensor would be atypical of the normal pattern of past daily temperature cycles of the same sensor, or other sensors in the same container, or sensors in geographically proximal containers); for simplicity, we use detection to describe both detection and deduction here. Based on past sensor data, mathematical models can be applied to automatically detect events such as a storage facility loading with commodity (when a fill level sensor is not present), commodity spoilage, smoldering fires, and commodity aerating/drying. When an event is detected, a notification message is displayed in the notifications panel (as described in connection with FIG. 1), the storage facility manager is notified (e.g., via email or in-app) and an annotation is automatically added.

The detection models could be based on statistical models (e.g., linear regression) or analytical equations with parameter fitting using optimization algorithms (e.g., Gradient Descent, Evolutionary algorithms) or other well-known machine-learning methods. Exemplary cases are presented in FIGS. 6, 7, and 8.

Figure 6:
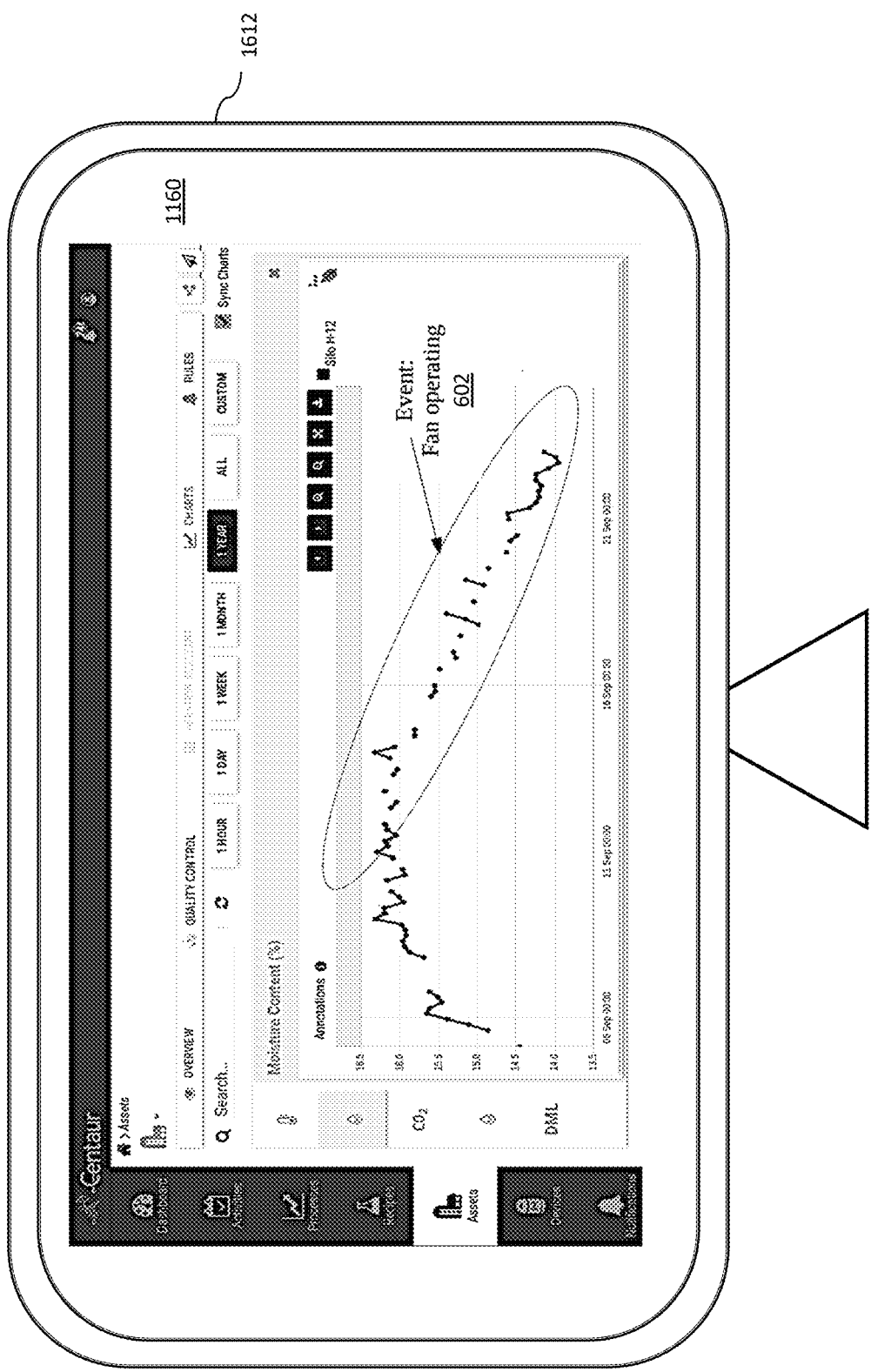
FIG. 6 depicts an exemplary user interface for a post-harvest monitoring system for presenting time courses of commodity moisture content in accordance with some embodiments of the invention; the time course shown covers an exemplary aeration initiation event.

FIG. 6 shows a user interface screen 1160 depicting time-course data of the quality metric Moisture Content. Starting around September 11 at 0:00 the values of moisture content decrease rapidly. The mathematical model detects the decrease and classifies it as a fan operating event 602.

Figure 7:
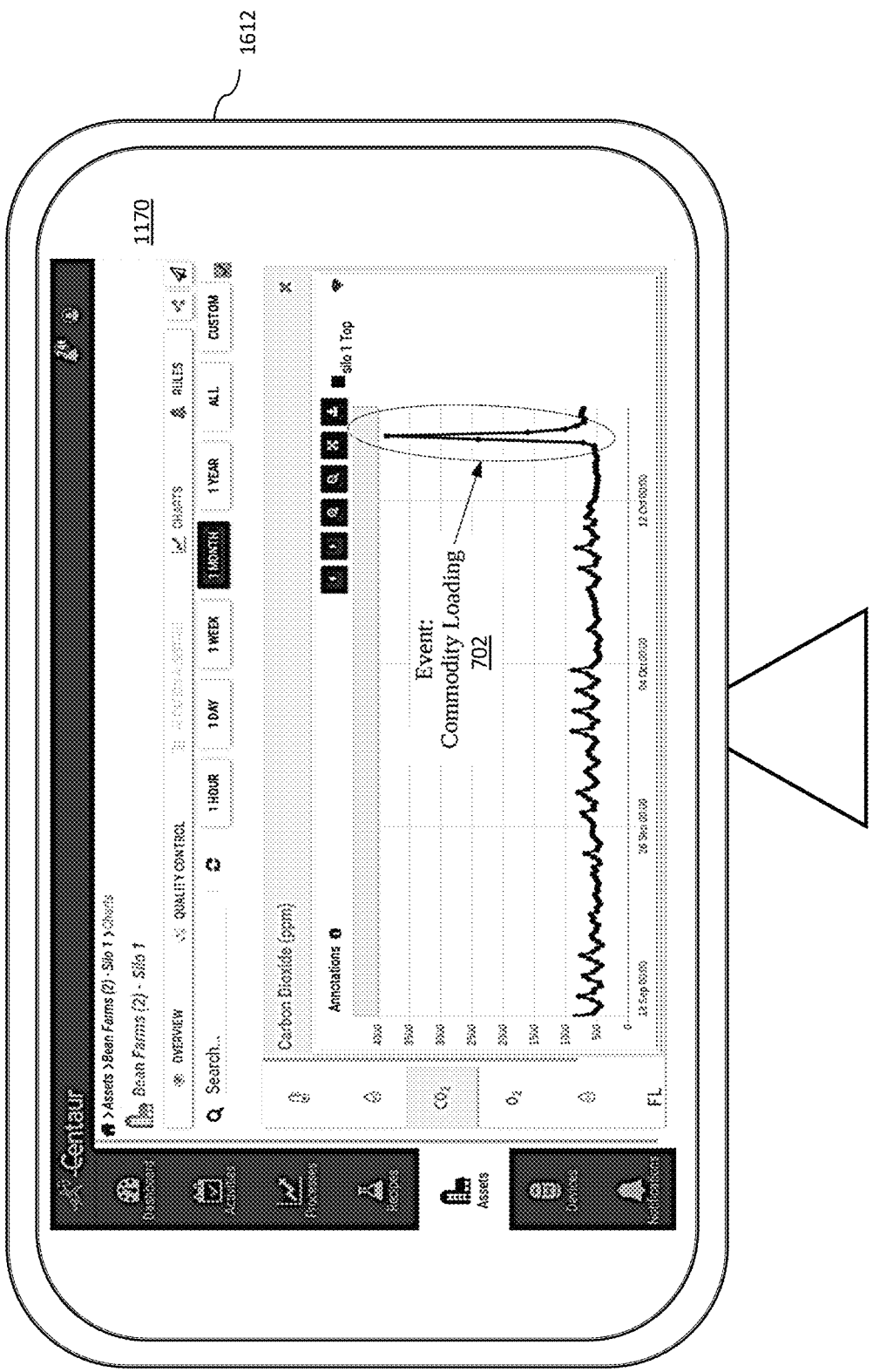
FIG. 7 depicts an exemplary user interface for a post-harvest monitoring system for presenting time courses of commodity $CO_2$ concentration in accordance with some embodiments of the invention; the time course shown covers an exemplary commodity loading event.
Figure 8:
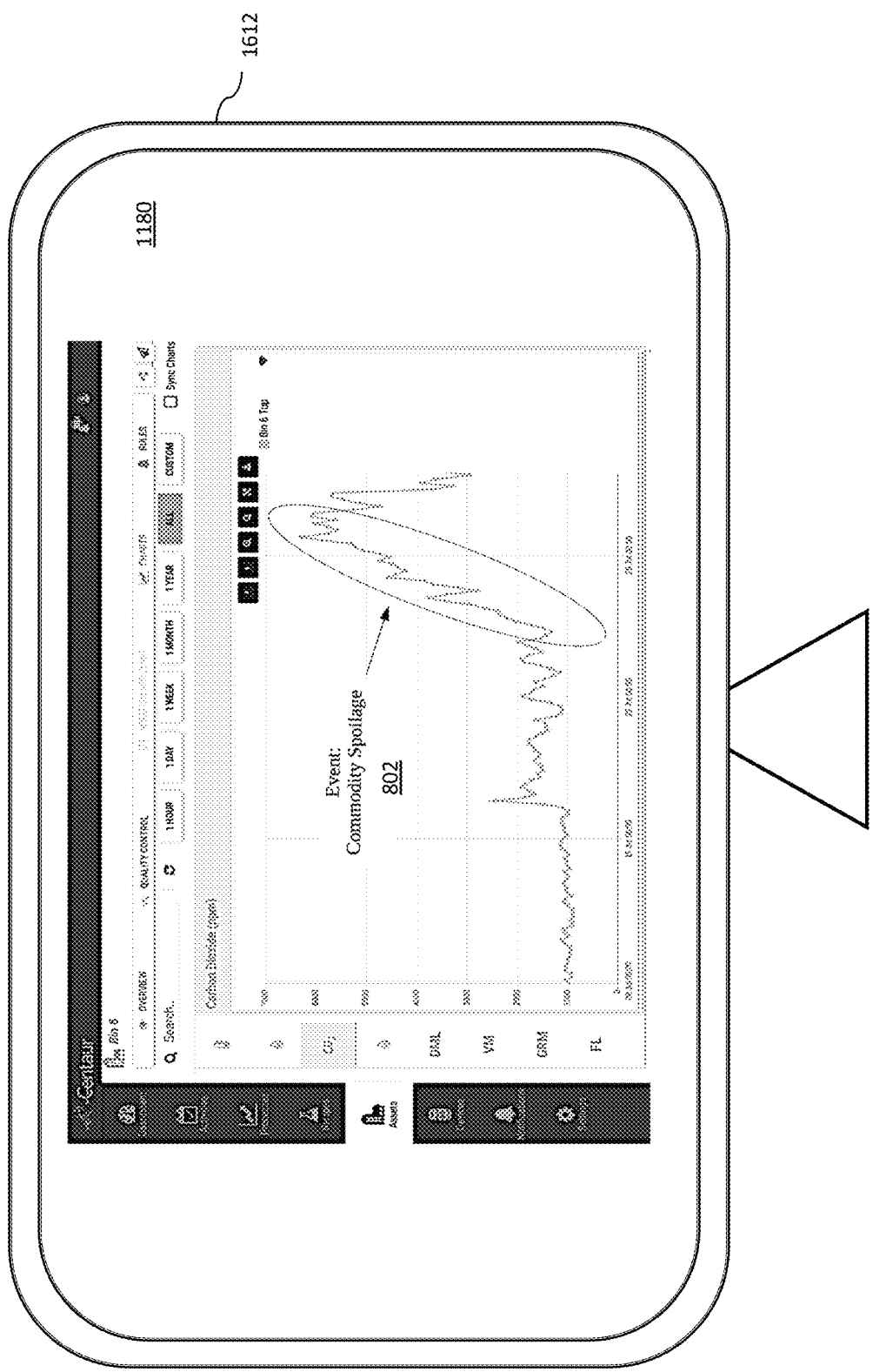
FIG. 8 depicts an exemplary user interface for a post-harvest monitoring system for presenting time courses of commodity $CO_2$ concentration in accordance with some embodiments of the invention; the time course shown covers an exemplary commodity spoilage event.

FIG. 7 shows a user interface screen 1170 depicting time-course data associated with $CO_2$ values. This screen is associated with another mathematical model, which detects sudden peaks in $CO_2$ time-course data values and classifies them as commodity loading events, e.g., 702.

Another event associated with $CO_2$ data is spoilage. In a user interface screen 1180 shown in FIG. 8, $CO_2$ values start to rise approximately on July 25 at 0:00 but with at a slower rate and with a different pattern than previously seen in the data depicted in FIG. 7. The underlying mechanisms that distinguish $CO_2$ spoilage from $CO_2$ loading events are described below, and when spoilage is determined, a commodity spoilage event 802 is indicated.

Spoilage Detection Based on $CO_2$ Data—Mathematical Model

The $CO_2$ values measured inside a storage facility are due to combination of multiple processes. Specifically, at every moment the $CO_2$ production rate is a function of the grain respiration, the insect respiration, and the $CO_2$ losses to the ambient environment:

$$R_{CO2,total} = R_{CO2,grain} + R_{CO2,insects} + R_{CO2,loss} \quad (E1)$$

According to a modified version of the White et al., (Intergranular carbon dioxide as an indicator of biological activity associated with the spoilage of stored wheat, Can. Agric. Eng. 24:35-42 (1982)) model, $R_{CO2,grain}$ (mg $CO_2$ per kg of grain in 24 hours) is a function of grain temperature T, moisture content MC and time in storage t. For example, the equation for wheat is as follows:

$$R_{CO2,grain} = pow(10, h_g(-4.054 + 0.0406T - 0.0165t + 0.0001t^2 + 0.2389MC)) \quad (E2)$$

where $h_g$ is a coefficient accounting for increased $CO_2$ rates due to mold presence. Thus, $h_g$ equals 1 in normal grain condition.

The prediction of insect population is based on a model described by Driscoll et al. (Prediction of insect populations in grain storage, Journal of Stored Products Research, Vol 36 (2) (2000)):

$$N(t)/dt = N_o r_m \exp(r_m t) \quad (E3)$$

$$r_m = f'(r.h.) \exp(c_1 T) + \ln[c_2(T_m - T)] \quad (E4)$$

$$f'(r.h.) = k_a + k_b r.h. + k_c r.h.^2 \quad (E5)$$

where $N(t)$ is the insect population at time t, $N_o$ is the initial (t=0) population size, $r_m$ is the rate of population increase which depends on both temperature T and relative humidity r.h; f'(r.h.) is a function describing the dependence of the population growth rate $r_m$ to relative humidity r.h., $T_m$ is the mortality temperature limiting population growth at temperatures near $T_m$, and $k_a$, $k_b$, $k_c$ $c_1$, and $c_2$ are constants. Coefficients $k_a$, $k_b$, $k_c$ $c_1$, $c_2$, and $T_m$ depend on the insect species. For example, for the Rhyzopertha Dominica the coefficients have the values $k_a$=0.1673, $k_b$=0.8477, $k_c$=−0.698, $c_1$=0.0607, $c_2$=0.01541, and $T_m$=39.50. $R_{CO2,insects}$ can be estimated from the insect population N(t) based on the data available in the scientific article of Emekci et al. (Respiration of stored product pests in hermetic conditions, In: Proceedings of the International Conference on Controlled Atmosphere and Fumigation in Stored Product (2001)).

The $CO_2$ losses to the environment are correlated to the $CO_2$ concentration inside the storage facility and the $CO_2$ concentration of the ambient environment:

$$R_{CO2,loss} = h(CO_{2,total} - CO_{2,amb}) \quad (E6)$$

where h is a coefficient showing the intensity of losses to the environment.

Figure 9:
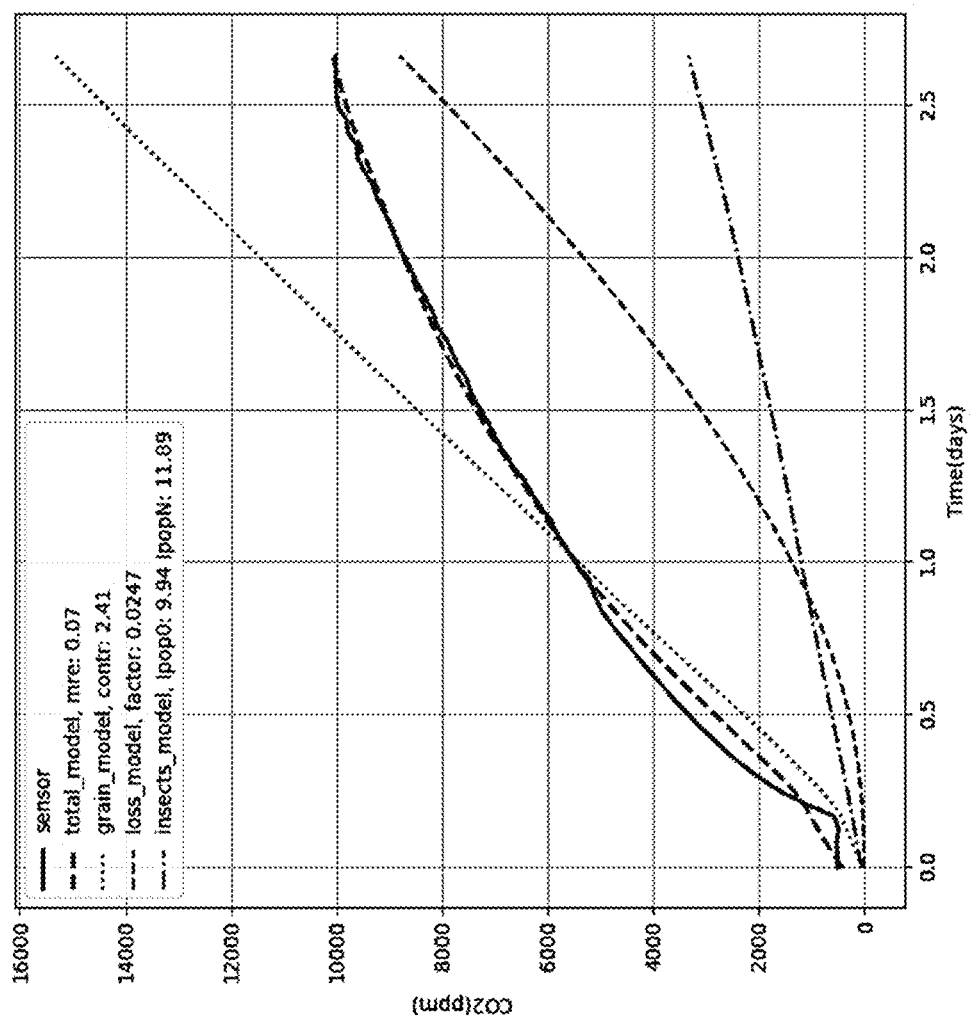
FIG. 9 is a graph depicting multiple time courses of commodity $CO_2$ concentration, including measured sensor data, individual model components, and the combined model that best fits the sensor data, in accordance with some embodiments of the invention.

Combining equations E1-E6 yields a system of equations in which some quantities are known (e.g., $k_a$, $k_b$, $k_c$ $c_1$, $c_2$, and $T_m$ are known because the pest species is specified by the user) or measured (e.g., T, $CO_{2,total}$), and some are unknown, namely $h_g$ (eq. E2), $N_o$ (eq. E3), and h (eq. E6). An optimization process searches for the "best" combination of values for the unknown quantities $h_g$, $N_o$, and h, by assuming $CO_{2,total}$ is also unknown and using equations E1-E6 to compute the value of $CO_{2,total}$ for each candidate combination of values for $h_g$, $N_o$, and h, and then comparing its deviation from the measured actual sensor value of $CO_{2,total}$; the search continues until this deviation is minimized or the optimization process fails to converge to a minimum deviation. FIG. 9 shows an example of how the optimization process analyzed the sensor $CO_2$ values and determined that the optimal values for the unknown quantities imply a large initial insect population (almost equal to 10 insects/kg grain) and that grain respirates 2.14 times more than normal. In this case, the storage facility manager may be notified by the system to apply immediate remediations such as fumigation, as grain condition (and therefore, marketability) seems to be deteriorating rapidly.

Safe Product Storage Time

Described next is an approach for predicting moisture content and temperature in a stored commodity using a numerical model combined with sensor data and/or ambient weather forecasts (whichever of said time-course data is available), further localizing the predicted values of moisture content and temperature at each three dimensional location within a storage facility, and further using the predicted moisture content and temperature to determine how long the commodity may continue to be safely stored in the same storage facility. For simplicity and without loss of generality, and without limiting the breadth of this invention for someone skilled in the art, the approach focuses on a specific class of commodities, namely grains, and a specific class of storage facilities, namely silos.

In order to analyze grain storage conditions and determine the change in concentration of $CO_2$ and temperature in silos, a mathematical model is used which combines and extends the models proposed by Barreto et al. (Analysis of storage conditions of a wheat silo-bag for different weather conditions by computer simulation, Biosystems Engineering 116, pp. 497-508 (2013)) and Lawrence et al. (Three-Dimensional Transient Heat, Mass, Momentum, and Species Transfer in the Stored Grain Ecosystem: Part I, Model Development and Evaluation. Transactions of the ASABE, 56(1): 179-188 (2013)). According to certain embodiments of the present invention, the model of Barreto is extended to include air movements and adapted to three dimensions from the prior two-dimensional model. Furthermore, in certain embodiments of the present invention, the model of Lawrence is extended to solve all the transfer equations of the storage structure walls as a porous medium. Due to commodity and insect respiration, $CO_2$ and temperature changes are both indicators for commodity spoilage. The mathematical model of equations (1)-(13) below takes into account the weather conditions locally and creates a coupled system in terms of intergranular air velocity (u), temperature T, grain moisture content W, oxygen $O_2$ and carbon dioxide $CO_2$ concentrations. Unlike the approaches in Barreto and Lawrence, implementations of the below model use a finite volume approach for discretizing constituent equations, incorporate an air flow component using the Navier-Stokes equation, and may incorporate a prediction of safe storage time based on germination loss models:

$$\nabla \vec{u} = 0 \tag{1}$$

$$\frac{\partial \vec{u}}{\partial t} + \frac{1}{\phi}\vec{u}\nabla\vec{u} = -\phi\nabla p + \nu\nabla^2\vec{u} - \phi\frac{\nu}{K}\vec{u} - \tag{2}$$

$$\phi\frac{F_e}{\sqrt{K}}|\vec{u}|\vec{u} + \phi g\beta(T - T_{ref}) + \phi g\beta_{Wg}(W_g - W_{g,ref})$$

$$\frac{\partial T}{\partial t} + \phi\frac{(\rho C_p)_f}{(\rho C_p)_{eff}}\vec{u}\nabla T = \tag{3}$$

$$\frac{k_{eff}}{(\rho C_p)_{eff}}\nabla^2 T + \frac{\rho_{eff}}{(\rho C_p)_{eff}}L_g\frac{\partial W_g}{\partial t} + \frac{\rho_{bs}}{(\rho C_p)_{eff}}q_H Y_{CO_2}$$

$$\rho_{bs}\frac{\partial W_g}{\partial t} + \frac{\eta}{R_v T_{abs}}\vec{u}\nabla W_g = \tag{4}$$

$$\nabla\left(\frac{D_v\varphi}{R_v\tau T}\eta\cdot\nabla W_g\right) + \nabla\left(\frac{D_v\varphi}{R_v\tau T}\omega\cdot\nabla T\right) - \frac{\omega}{R_v T}\vec{u}\nabla T + \rho_{bs}q_w Y_{CO_2}$$

$$\phi\frac{\partial CO_2}{\partial t} + \phi\vec{u}\nabla CO_2 = \phi\frac{D_{CO_2}}{\tau}\nabla^2(CO_2) + \phi\rho_{eff}CO_2 \tag{5}$$

$$\phi\frac{\partial O_2}{\partial t} + \phi\vec{u}\nabla O_2 = \phi\frac{D_{O_2}}{\tau}\nabla^2(O_2) + \phi\rho_{eff}O_2 \tag{6}$$

Respiration may be modelled by the complete combustion of a typical carbohydrate. The rate of $CO_2$ production $R_{CO2}$ in $m^3\ s^{-1}\ kg^{-1}$ [dry matter] is given by:

$$r_{CO_2} = \frac{Y_{CO_2}}{1000}\frac{RT}{M_{CO_2}}\frac{r_{O_2}}{P_{at}} = r_{CO_2} \tag{7}$$

The boundary conditions related to the above equations (1)-(7) are given by:

$$-k_b\frac{\partial T}{\partial t} = h_c(T - T_{amb}) - \alpha G + \xi\sigma(T^2 - T_{sky}^4) \tag{8}$$

$$\sigma T_{sky}^4 = \xi_{sky}\sigma T_{amb}^4 \tag{9}$$

$$T = T_{soil}(y, t) = T_1(y) + T_2 \exp\left(-y\sqrt{\frac{2\Psi}{D_{soil}}}\right)\left[\cos\left(\Psi t - y\sqrt{\frac{2\Psi}{D_{soil}}} - \varphi\right)\right] \tag{10}$$

$$\frac{\partial p_u}{\partial n} = 0 \Rightarrow \eta D_w\frac{\partial W_g}{\partial n} = -\omega D_w\frac{\partial T}{\partial n} \tag{11}$$

$$-D_{CO_2}\frac{\partial CO_2}{\partial n} = \frac{P_{CO_2}P_{atm}}{L}(CO_2 - CO_{2out}) \tag{12}$$

$$-D_{O_2}\frac{\partial O_2}{\partial n} = \frac{P_{O_2}P_{atm}}{L}(O_2 - O_{2out}) \tag{13}$$

The above boundary conditions (8)-(13) take into account solar radiation and convection to the surroundings, as well as the interaction between the soil and the bottom layer of the storage facility (e.g., silo). Gas transfer through the plastic layer is modelled by defining an equivalent permeability of the plastic to $O_2$ and $CO_2$. Plastic is assumed impermeable to moisture transfer.

The values of some parameters which may be used as input to the model can deviate from their typical values. For instance, thermal conductivity of a metal silo may vary due to corrosion or paint. This issue is overcome in embodiments by using real-time sensor data. As the storage period advances, model predictions are compared with sensor data at the locations where sensors are installed (specified as points in a three-dimensional space). An iterative optimization process for the input parameter values based on the measured sensor data may be employed to determine any changes in the input parameter values which improve the agreement between the model and sensor data. The outcome of this optimization process is a more accurate model prediction not only applicable to the specific sensor location(s) but by inference also applicable on the entire storage volume.

Figure 10:
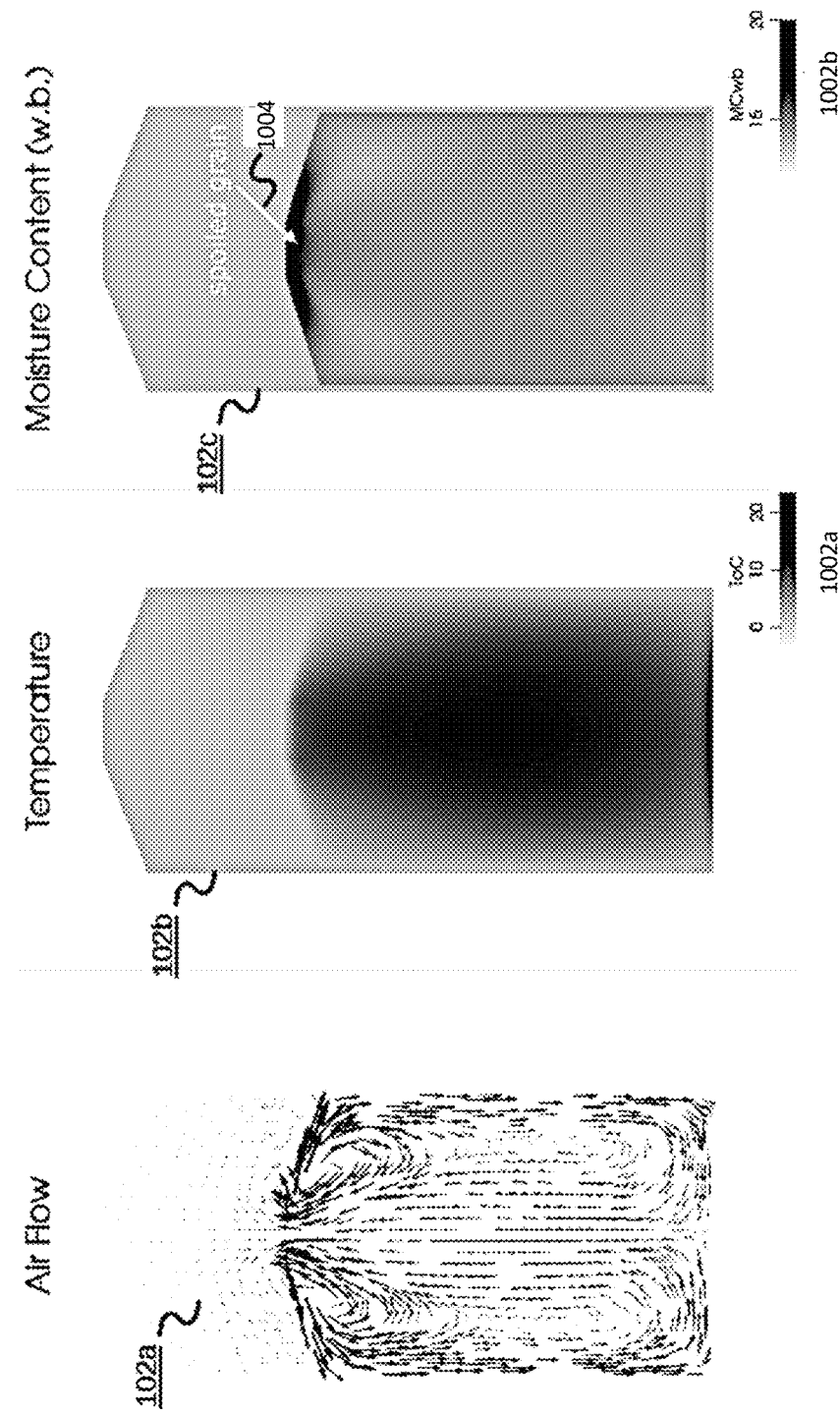
FIG. 10 depicts representations for presenting air flow, temperature, and moisture levels within a user interface for a post-harvest monitoring system for a stored commodity in accordance with some embodiments of the invention.

Among the capabilities of embodiments of the models described here, such as that of equations (1)-(13), is the prediction of areas inside the commodity (e.g., grain bulk) with moisture condensation due to temperature difference between the grain and ambient conditions (see FIG. 10, describing moisture migration in bulk grain leading to mold damage near the surface according to the forecast of the mathematical model).

Particularly, as the ambient temperature drops during the cool season, the surface (and peripheral) layers of the grain become considerably cooler than the internal grain mass. Temperature gradients are established in the grain bulk which create convection currents that circulate air through the intergranular spaces. The cold dense air settles along the outer walls, and the warmer air (which contains more moisture than cool air) moves upward toward the colder upper surface of the grain bulk. In this way, moisture carried by warm air may "migrate" to cooler surface grain where the air cools to a "dew point" and deposits excess moisture, slowly increasing the grain moisture content in the upper parts of the grain bulk. In some cases, condensation of water may occur on those areas, causing rapid mold (and sometimes bacterial) spoilage. See, e.g., Navarro and Noyes, The Mechanics and Physics of Modern Grain Aeration Management. CRC Press, London (2002). FIG. 10 shows three different versions of storage facility representations 102 (102a, 102b, 102c). The storage facility representations in FIG. 10 may represent any physical storage facility containing a commodity, such as a silo containing grain. A storage facility representation 102 may be depicted as a two-dimensional slice of a storage facility or a plane within a storage facility, e.g., as shown with storage facility representations 102a, 102b, and 102c.

Exemplary storage facility representation 102a shows air flow at locations within a two-dimensional plane of the storage facility at a time point, representing flow using arrows that indicate direction and magnitude of the flow. Air flow may be increased as a result of mechanical aeration of the commodity. Exemplary storage facility representation 102b shows temperature at locations within a two-dimensional plane of the storage facility at a time point and is additionally associated with legend 1002a which indicates a range of colors corresponding to a range of degrees Celsius. Exemplary storage facility representation 102c shows moisture content at locations within a two-dimensional plane of the storage facility at a time point, and is additionally associated with legend 1002b which indicates a range of colors corresponding to a range of moisture content values (where MCwb indicates the moisture content is computed using a wet basis (%): MCwb=100*MCdb/(100+MCdb), and MCdb indicates moisture content computed using a dry basis (%): MCdb=100*MCwb/(100-MCwb)).

Storage facility representation 102c additionally includes a spoilage indicator 1004 (e.g., shown as an arrow identifying a region predicted to correspond to spoiled commodity). In certain embodiments, a spoilage indicator 1004 may be shown at a represented location in storage facility representation 102 when a portion of the commodity associated with the location of the storage facility representation is associated with a quality metric value that exceeds a spoilage threshold at the time point depicted in the storage facility representation 102. In certain embodiments, storage facility representation 102 shows simulated or forecasted data (e.g., values for a quality metric computed using a simulation), and in certain embodiments, storage facility representation 102 shows actual current or historical measurements (or values based on same), e.g., based on measurements using a weather service or one or more sensor devices placed within the storage facility.

Figure 11:
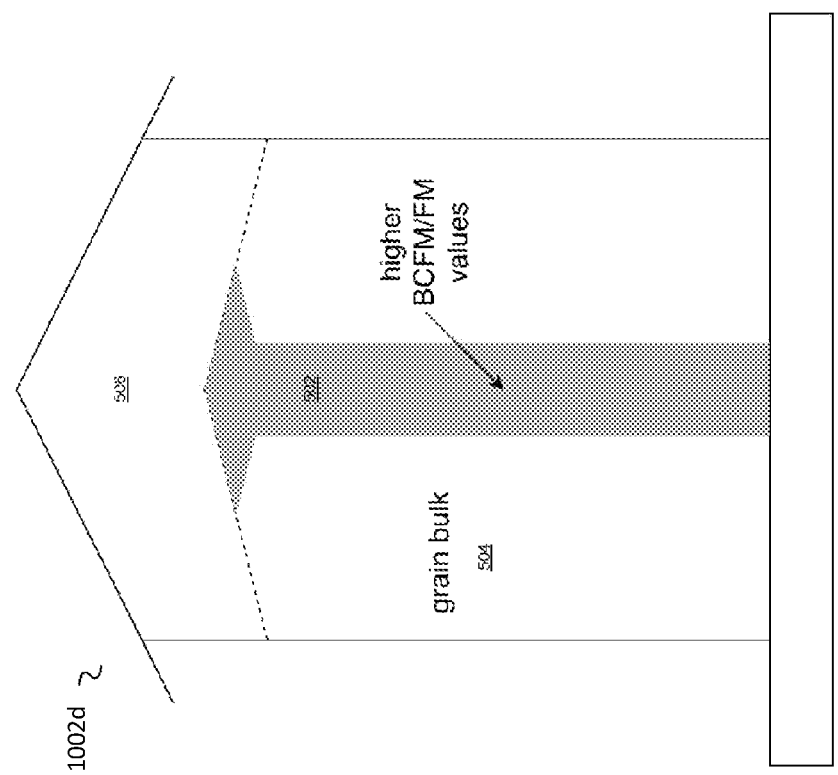
FIG. 11 depicts a representation for presenting Broken Corn and Foreign Materials/Foreign Materials information for a commodity within a user interface for a post-harvest monitoring system in accordance with some embodiments of the invention.

Occasionally, stored grain kernels may be prone to breaking during handling, loading and unloading. Additionally, grain may be mixed with foreign materials from the field. These anomalies are usually referred to collectively as Broken Corn and Foreign Materials (BCFM) for corn or Foreign Materials (FM) for other commodities. BCFM/FM percentages of 1% to 3% are typical in commercial grain stores. One of the adverse effects of BCFM/FM is that it usually accumulates at the center of mass of grain hindering the movement of intergranular air currents and creating pockets of increased moisture that are favorable to the formation of mold, fungi and insects. Further improvements of the proposed methods are achieved by modeling the adverse effects of areas with higher BCFM/FM values. In a preferred embodiment, BCFM/FM effects are modeled by adapting the properties of a portion of the grain mass (e.g., decreasing the porosity, increasing flow resistance) that are used in the computations disclosed herein. A user of the methods may interact with these aspects by adjusting the preferred values of BCFM/FM in the system and selecting a profile of the area of BCFM/FM accumulation via the user interface (see FIG. 11). Aspects of the profile or an alternative specification of the BCFM/FM values for a storage facility may be displayed using a storage facility representation 102d as shown in FIG. 11, in which a region of a storage facility associated with higher BCFM/FM values 502 is displayed with a contrasting appearance (e.g., a different color) compared to regions of the storage facility containing a commodity that are associated with typical or minimal BCFM/FM values 504, or regions that do not contain a commodity 506. In certain embodiments, a profile may be specified using an interactive storage facility representation 102 for specifying the dimensions or general region containing the higher BCFM/FM values, e.g., by selecting the corresponding borders of the high BCFM/FM region in a two-dimensional graphical representation of the storage facility via a graphical user interface.

Coring

Figure 12:
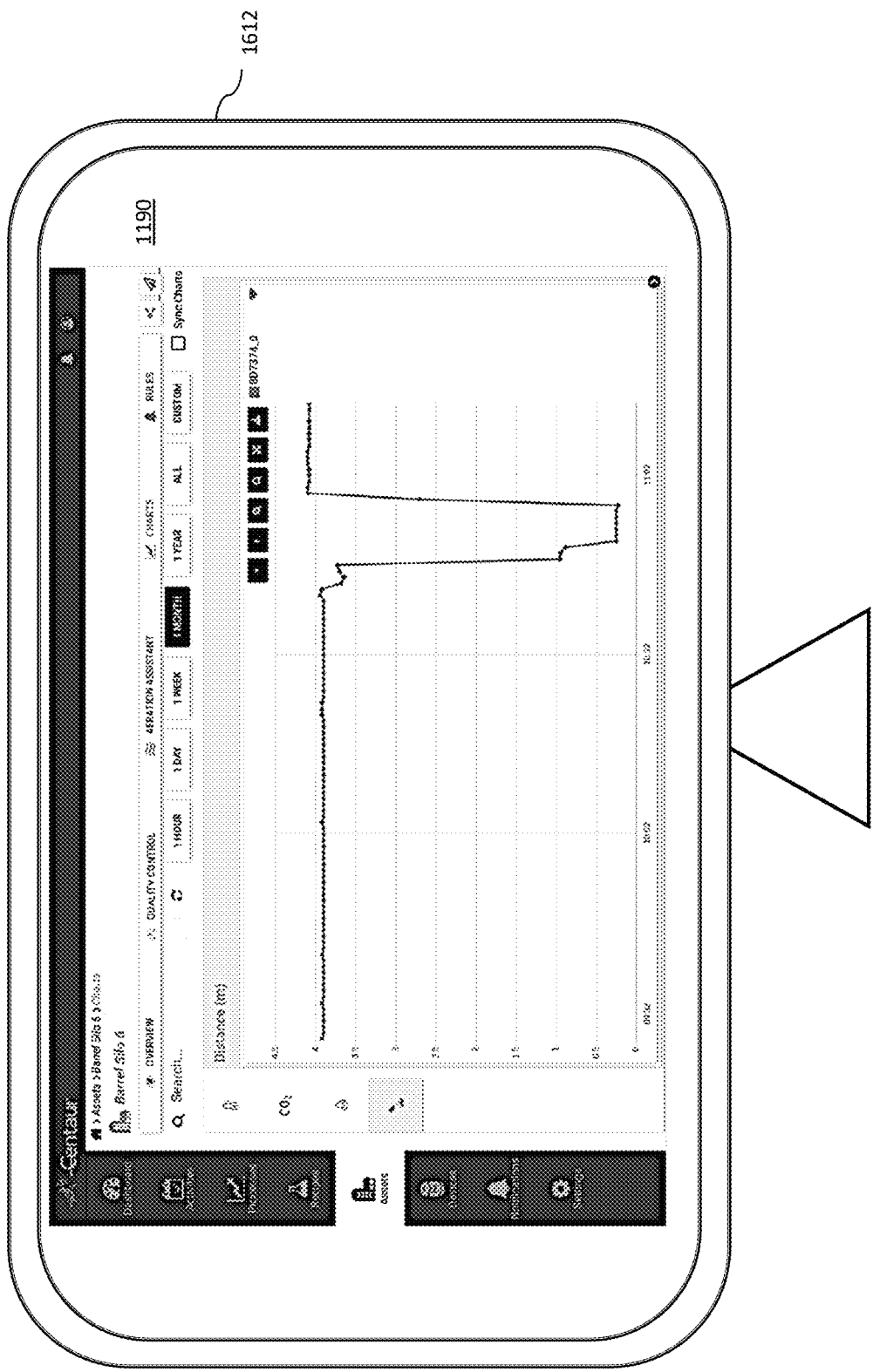
FIG. 12 depicts an exemplary user interface for a post-harvest monitoring system for monitoring and managing stored commodity quantity in accordance with some embodiments of the invention.

The coring operation consists of removing the center portion of the grain mass, or core of the stored product, to improve airflow distribution. An additional benefit of this practice is the elimination of a portion of the BCFM/FM material, which is a source of fungal inoculum and feed for insects. Coring is typically performed after filling the storage facility with a commodity or when high levels of temperature, moisture content or $CO_2$ concentrations are detected. According to the invention, when a storage facility manager decides to perform a coring process based on the detected conditions, the fill level sensor can provide precise information about the current levels of the commodity in the storage facility and the amount of commodity to be removed. User interface 1190 of FIG. 12 provides the ability to sort and display time-course data of the fill level sensor in real-time.

Commodity Aeration Management

Aeration of a commodity is the most common procedure to improve and sustain the condition of commodities such as bulk grain in storage. Aeration is achieved by moving ambient or refrigerated air through a grain bulk until a new microclimate is produced that will prevent stored grain deterioration. Parameters affecting the planning of the aeration process include, among others, aeration time, energy consumption, grain deterioration, target grain temperature and moisture content, and ambient weather conditions. The main objectives of the aeration process are: the cooling of the grain bulk, equalizing temperature throughout the grain bulk, preventing biological heating in damp grain, and removing odors and fumigant residues (see Navarro and Noyes (2002)). Described next is an approach for predicting moisture content and temperature in stored commodity extending the one presented above by incorporating modeling of grain aeration. For simplicity and without loss of generality, and without limiting the breadth of this invention for someone skilled in the art, the approach focuses on a specific class of commodities, namely grains, and a specific class of storage facilities, namely silos.

The equations that describe the aeration mathematical model are the following:

$$\frac{\partial T}{\partial t}\left\{\rho_b[C_{p,grain}+C_{p,water}W_g]+\varphi\rho_a\left[C_{p,air}+h\left(C_{p,water}+\frac{dh_v}{dT}\right)\right]\right\}= \quad (14)$$

$$h_s\rho_b\frac{dW_g}{dt}-u_a\rho_a\left[C_{p,air}+h\left(C_{p,water}+\frac{dh_v}{dT}\right)\right]\nabla T+$$

$$k_{eff}\nabla^2 T+\rho_b\frac{dm_s}{dt}(Q_r-0.6\,h_v)$$

$$\frac{\partial W_g}{\partial t}+\frac{u_a\rho_a}{\rho_b}\nabla h=\frac{\rho_a}{\rho_b}D_{eff}\nabla^2 h+\frac{dm_s}{dt}0.6(1+1.66\,W_g) \quad (15)$$

where $h_v = 2501330 - 2377 * T$ and $$h_s = h_v\left(1+\frac{A\exp(-B\,W_g)}{(T+C)^2}(T+273.15)\times\left(-5+\frac{6800}{T+273.15}\right)\right).$$

$\frac{dh_v}{dT}=-2377$ is the differential of latent heat with respect to temperature and $h$ is the humidity ratio of air:

$$h=\frac{0.622\,p_{sat}r.h.}{P_{atm}-p_{sat}r.h.} \quad (16)$$

The empirical relationship between the saturation vapor pressure ($p_{sat}$) of water and temperature is:

$$p_{sat}=\frac{6\times10^{25}}{(T+27315)^5}\exp\left(-\frac{6800}{T+273.15}\right) \quad (17)$$

whereas the relative humidity (r.h.) of the intergranular air is found from:

$$r.h. = \exp\left(-\frac{A}{T+C}\exp(-BW_g)\right) \quad (18)$$

Coefficients A, B and C are dependent on the commodity.

In order to determine the rate of dry matter loss in maize the empirical equations developed by Thompson (Temporary Storage of High-Moisture Shelled Corn Using Continuous Aeration. Transactions of the ASAE, 15(2), 333-337 (1972)) and described by Navarro and Noyes (2012) are used:

$$\frac{dm_s}{dt}=\frac{14.72\times10^{-10}\{\exp(1.667\times10^{-6}t_p)-1\}+2.833\times10^{-9}}{M_M M_T} \quad (19)$$

where $$t_p=\frac{t}{M_M M_T}$$

and $M_M$ and $M_T$ modify the grain conditions depending on its moisture content and temperature respectively.

When $T \leq 15.5°$ C. or $MC_{wb} \leq 19\%$:

$$M_T = 32.2\exp(-0.1044T-1.856) \quad (20)$$

When $T > 15.5°$ C. or $19 < MC_{wb} \leq 28\%$:

$$M_T = \quad (21)$$
$$32.2\exp(-0.1044\,T-1.856)+\left(\frac{MC_{wb}-19}{100}\right)\exp(0.0183\,T-0.2847)$$

When $T > 15.5°$ C. or $MC_{wb} > 28\%$:

$$M_T = 32.2\exp(-0.1044T-1.856)+0.09\exp(0.0183T-0.2847) \quad (22)$$

The moisture modifier is given by the expression:

$$M_M = 0.103\left\{\exp\left(\frac{455}{MC_{db}^{1.53}}\right)-0.00845\,MC_{db}+1.558\right\} \quad (23)$$

Figure 13:
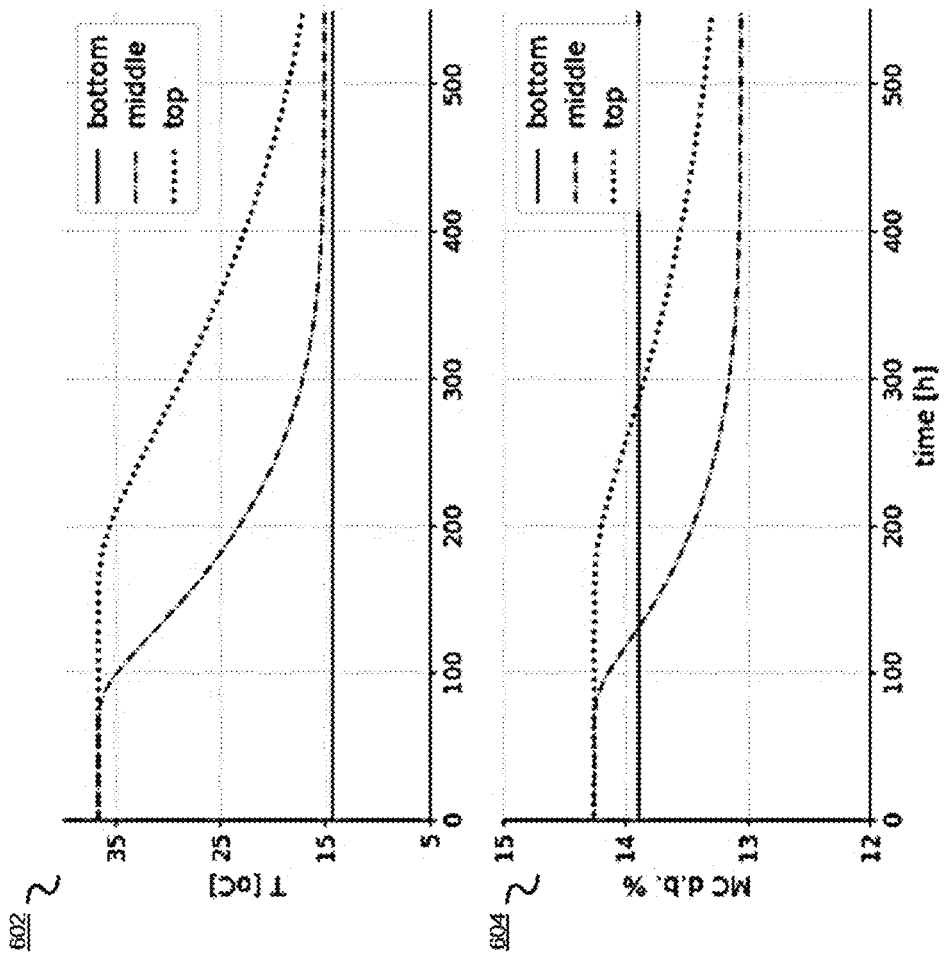
FIG. 13 depicts graphs of time courses of commodity temperature and moisture content at a set of locations in accordance with some embodiments of the invention.

The simulation model considers the storage facility dimensions, commodity (e.g., grain) condition, aeration fan characteristics (e.g., size, air flow rate), and weather conditions to provide a custom-made prediction of the process outcome. In one example, FIG. 13 presents the time evolution of grain temperature (602) and moisture content (604, where MC d.b. indicates moisture content, dry basis) at three different vertical locations of a silo (bottom, middle, top). In certain embodiments, the graphs 602 and 604 represent the values of temperature and moisture content as time-course data computed using a simulation model as described here. Using this numerical method, a silo or other storage facility manager can evaluate critical aspects, such as operating fan hours and the homogeneous distribution of grain temperature. The simulation model incorporates a representation of intergranular air movements created by temperature gradients (convection currents), which may lead to moisture condensation and rapid mold development. For example, the model may be used to predict the effect of aeration (e.g., generated by one or more fans associated with a size and air flow rate) over a period of time (fan hours) in a particular storage facility. Simulations of a particular storage facility using a range of fan characteristics (e.g., based on the existing number of fans at existing locations and a low or default fan speed (air flow rate), or increasing the number or size of the fans, changing the locations of fans, or changing the fan speeds) and simulating the commodity conditions for a period of time may be used to predict the fan arrangement and time period (fan hours) needed to reduce commodity moisture and/or temperature (or temperature gradients) to below threshold values for optimal or safe storage. Such an approach may provide the minimum fan operation hours for achieving an optimal storage condition. For example, information such as the fan arrangement and the elapsed time in the simulation at which all locations within the commodity are associated with one or more quality metrics within an acceptable safe storage range may be used by a storage facility manager to configure aeration of a particular commodity in a particular storage facility.

Automatic Control

In case the storage facility aeration fans are connected with an automatic controller, the system is able to automatically act on its predictions and recommendations for remediation and initiate an optimized aeration process (reduced fan running times) thus lowering operating costs and energy consumption. In certain embodiments, the system may be scheduled to compute a forecast of the commodity temperature (or temperature gradients) and moisture content in a storage facility on a regular schedule. Such a forecast may be computed using a CFD simulation that incorporates third party weather forecast data (e.g., predicted temperature, wind speed, humidity) for the geographic location of the storage facility. The system may identify a predicted alert condition for commodity temperature and/or moisture content at a future time point using the temperature/moisture content forecast. The system may compute an optimal aeration program based on fan characteristics to address the alert condition based on, e.g., a CFD simulation. The system may configure and initiate an aeration program at a forecasted time point (e.g., an optimized aeration process, during which certain fans are activated at a certain fan speed at a certain time) to address the forecasted alert condition. In certain embodiments, the system may compute and initiate an optimal aeration program using the lowest number of fan operation hours based on a currently detected alert condition (e.g., when sensor devices detect that the current temperature, temperature gradients, or moisture content of the commodity is outside of an acceptable range at sampled locations within the storage facility).

For example, if the geographic temperature at the location of a grain silo is predicted to increase by 5 degrees Celsius in 36 hours, this may affect the temperature gradient of the grain stored within the silo and lead to a scenario where spoilage of the grain is imminent. A model simulation may be used to determine the effect of the geographic temperature change on quality metrics, and also to determine the optimal aeration process for minimizing or eliminating the effect on the quality metrics—e.g., by determining how long to activate the fans within the silo to compensate for the geographic temperature increase.

In certain embodiments, the system may employ business metrics in addition to quality metrics in determining the optimal aeration program; business metrics may include the varying cost of electricity (or other form of available energy), which may favor operating fans and heat exchange (A/C) equipment at nighttime when electricity is cheapest and ambient temperature is lowest (requiring less A/C power to achieve the same cooled air temperature), in which case, e.g., the optimal program may operate the fans and heat exchange equipment over 4 successive 10 pm-4 am sessions, by contrast to a single, continuous 24 h session, to achieve some desired target grain conditions. Additional metrics may include sustainability targets and constraints, such as meeting a specific greenhouse gas emission budget with respect to the energy expended for grain aeration and conditioning, by enforcing an energy or emission constraint which can be then translated to a maximum operating hours constraint for optimizing the schedule of one or multiple aeration fans, in one or multiple storage facilities.

Figure 14:
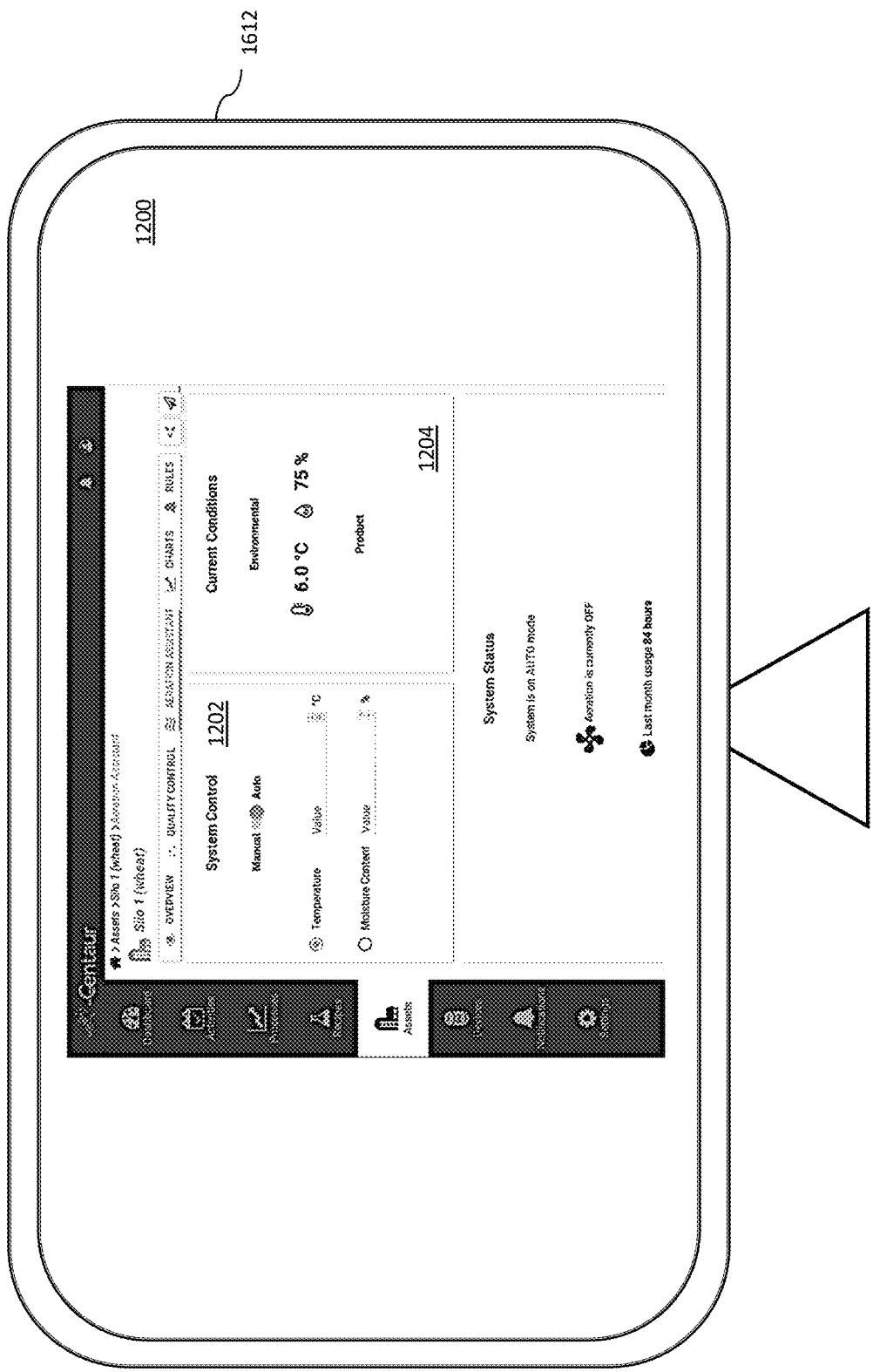
FIG. 14 depicts an exemplary user interface for a post-harvest monitoring system for monitoring and managing the aeration process of a stored commodity in accordance with some embodiments of the invention.

FIG. 14 shows exemplary user interfaces 1200 for monitoring and managing the aeration process of a stored commodity, e.g. for display at a user device such as a personal computer or smartphone.

User interface 1200 of FIG. 14 includes a navigation panel 1202 for toggling between the manual and the automatic mode. As stated above, if the automatic mode is selected, the user can define the desired grain conditions and the system will select the optimum time interval to operate the aeration fan. User interface 1200 of FIG. 14 includes an information panel 1204 of the current weather conditions as well as whether the system is in automatic mode, if the aeration fan is currently operating, and the total fan operating hours during the last month.

Commodity Storage Management Using a Monitoring and Modeling Platform

Figure 15:
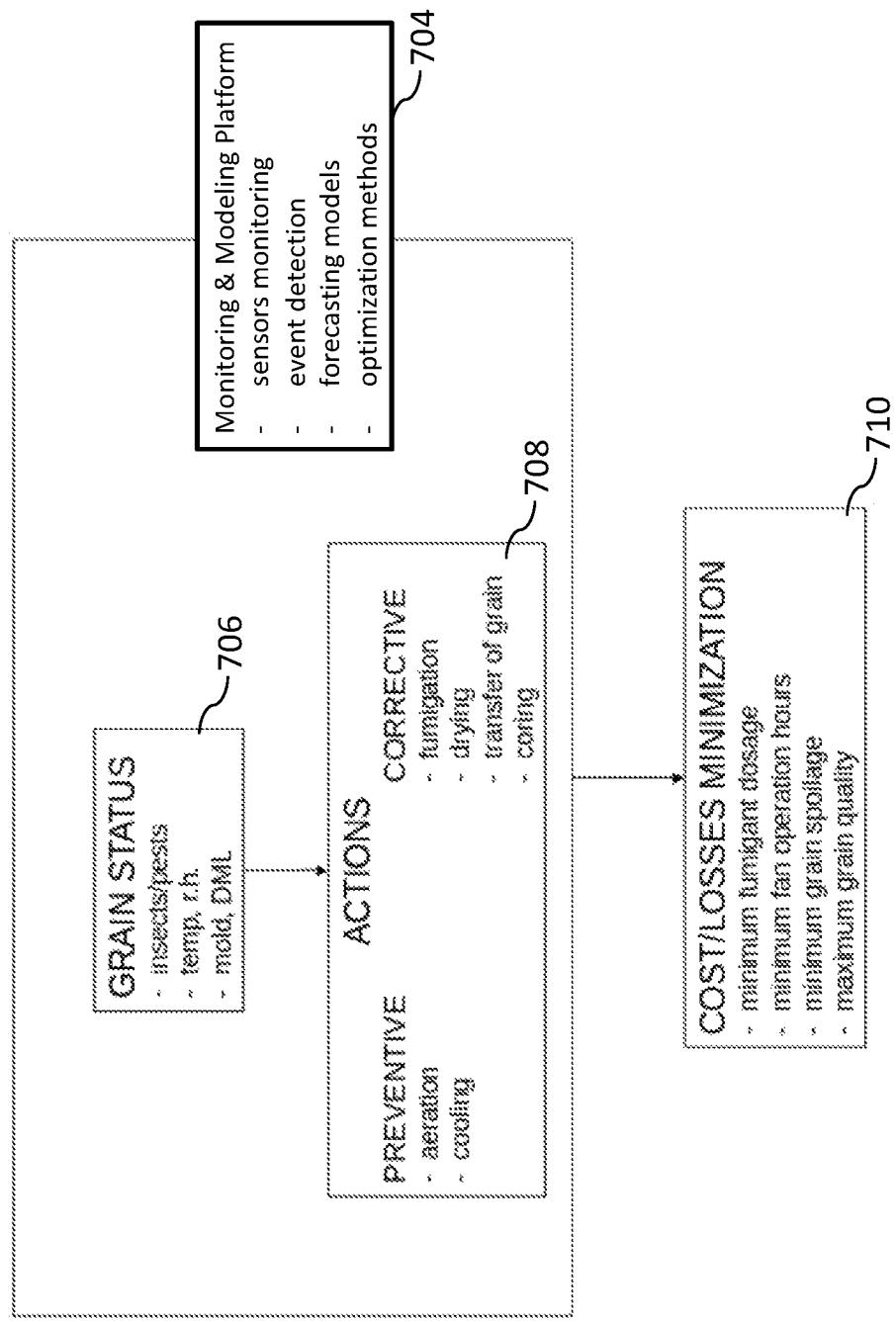
FIG. 15 depicts coordinated processes for a post-harvest monitoring system for monitoring stored commodity quality status and taking preventive or corrective actions in order to minimize cost and commodity loss, in accordance with some embodiments of the invention.

FIG. 15 shows coordinated processes 702 for minimizing the operation costs and grain losses in a storage facility using platform features (e.g., platform 704, which may include wireless contact, e.g., temperature, and non-contact, e.g., fill level, sensor devices for monitoring past and current actual quality and business metrics inside a commodity storage facility; computation of derived quality and business metrics, e.g., moisture level and value of commodity; incorporation of third-party metrics, e.g., ambient temperature; automatic detection of current known or unknown events, e.g. spoilage, grain loading, and aeration fan operating; forecasting models for the values of quality or business metrics at future time points and under various conditions using, e.g., CFD, and optimization methods for, e.g., computing or predicting the optimal conditions and interventions or treatments). Specifically, the predictive capabilities of the platform, with the simultaneous use of, e.g., wireless sensor devices (e.g., edge devices), offer an in-depth knowledge of the current and future commodity status 706 (level of infestation by insects or other pests, temperature and moisture content or relative humidity distributions, mold presence, dry matter loss rates) throughout the storage space and time period. Detection or prediction of a quality or business metric that is currently or is forecasted to be outside of an acceptable range (e.g., that may result in spoilage) may be used to immediately take a preventive or corrective action, or to schedule such an action 708 at a future point in time. In certain embodiments, the preventive or corrective actions of a storage facility manager may be guided by the information provided by the platform. In certain embodiments, preventive or corrective actions may be automatically initiated (e.g. configured and scheduled for a current or future point in time) by the platform as a result of commodity status reporting 706. As a result, each one of these actions can be optimized to the user benefit resulting in cost and loss minimization 710 (prevention of crop spoilage, improved commodity quality, lower operating costs, etc.).

Figure 16:
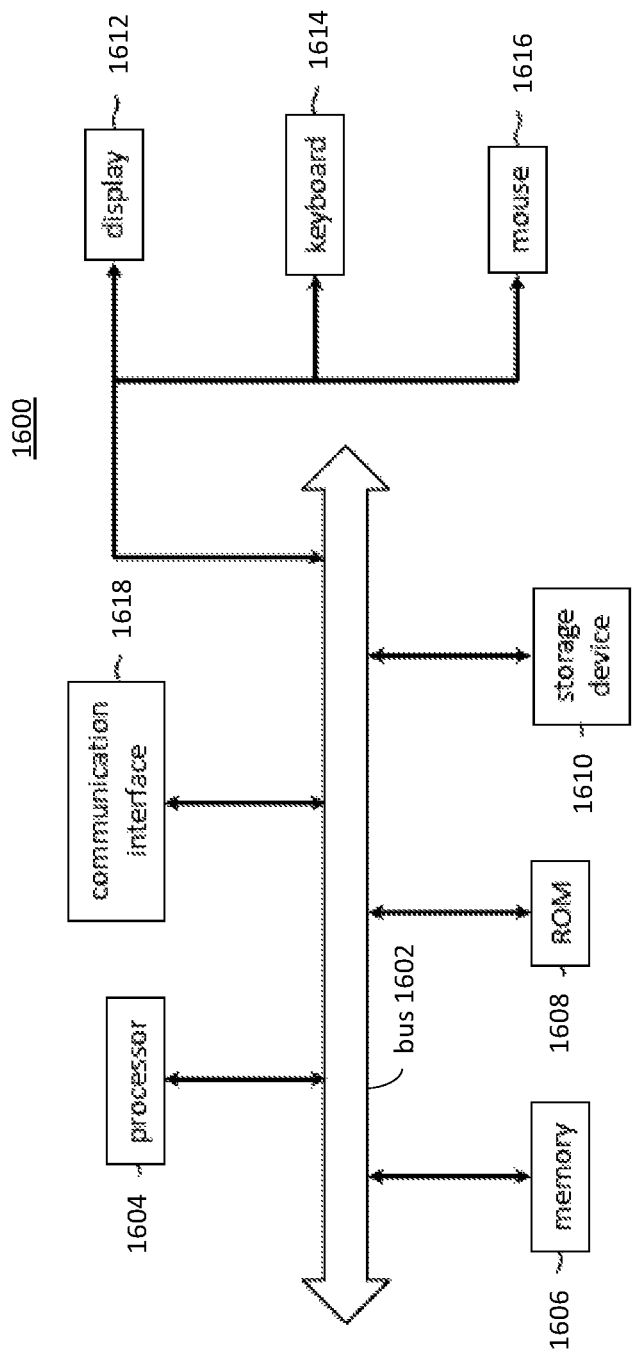
FIG. 16 shows an example of a computer system configurable as a post-harvest monitoring system in accordance with some embodiments of the invention.

Referring to FIG. 16 an example of a computer system 1600 is illustrated. Computer system 1600 may be implemented as a processor-based system with a processor-readable storage medium having processor-executable instructions stored thereon so that when the processor executes those instructions it performs operations to cause the actions described above. For example, platform 704 may execute on or include one or more computer system(s) 1600. Computer system 1600 includes a bus 1602 or other communication mechanism for communicating information, and a processor 1604 (e.g., a microprocessor) coupled with the bus 1602 for processing information. Computer system 1600 also includes a main memory 1606, such as a random access memory (RAM) or other dynamic storage device, coupled to the bus 1602 for storing information and instructions to be executed by processor 1604. Main memory 1606 also may be used for storing temporary variables or other intermediate information during execution of instructions to be executed by processor 1604. Computer system 1600 further includes a read only memory (ROM) 1608 or other static storage device coupled to the bus 1602 for storing static information and instructions for the processor 1604. A storage device 1610, for example a hard disk, flash memory-based storage medium, or other storage medium from which processor 1604 can read, is provided and coupled to the bus 1602 for storing information and instructions (e.g., operating systems, applications programs, and the like).

Computer system 1600 may be coupled via the bus 1602 to a display 1612, such as a flat panel display, for displaying information (such as the above-described user interface screens and elements) to a user. An input device 1614, such as a keyboard including alphanumeric and other keys, may be coupled to the bus 1602 for communicating information and command selections to the processor 1604. Another type of user input device is cursor control device 1616, such as a mouse, a trackpad, or similar input device for communicating direction information and command selections to processor 1604 and for controlling cursor movement on the display 1612. Other user interface devices, such as microphones, speakers, etc. are not shown in detail but may be involved with the receipt of user input and/or presentation of output.

Computer system 1600 also includes a communication interface 1618 coupled to the bus 1602. Communication interface 1618 may provide a two-way data communication channel with a computer network, which provides connectivity to and among the various computer systems discussed above. For example, communication interface 1618 may be a local area network (LAN) card to provide a data communication connection to a compatible LAN, which itself is communicatively coupled to the Internet through one or more Internet service provider networks. The precise details of such communication paths are not critical to the present invention.

While the preferred embodiments have been shown and described, it will be understood that there is no intent to limit the invention by such disclosure, but rather, is intended to cover all modifications and alternate constructions falling within the spirit and scope of the invention.

What is claimed is:

1. A post-harvest monitoring system, comprising a processor and a memory communicably coupled to the processor, the memory storing processor-executable instructions, which instructions, when executed by the processor, cause the processor to perform steps, comprising:
   receiving sensor device measurements from a plurality of sensors deployed within a commodity storage facility, various ones of said sensors being co-located with portions of a stored commodity in the storage facility, said sensor device measurements including temperature, relative humidity, air flow, and gas concentration within the commodity storage facility and being received as time-course data streams;
   predicting a safe storage time for said stored commodity within said commodity storage facility using a numerical model combined with said sensor device measurements, said mathematical model adapted to treat walls of said commodity storage facility as a porous medium and incorporating an air flow component using a Navier-Stokes equation; and
   presenting, as a user interface screen for the post-harvest monitoring system on a display communicably coupled to the processor, a predicted safe storage time for said commodity along with a representation of the storage facility to include locations of the sensor deployed therein and some or all of air flow, temperature, or moisture content within the storage facility and/or the stored commodity, and stored commodity quality metrics predictions and/or stored commodity business metrics predictions.

2. The post-harvest monitoring system of claim 1, wherein predicting the safe storage time for said stored commodity within said commodity storage facility comprises:
   determining, by the processor of the post-harvest monitoring system according to the processor-executable instructions stored in the memory, a portion safe storage time for each portion of a plurality of portions of the stored commodity in the storage facility, said determining based on the sensor device measurements and a linear model or exponential model for dry matter loss, mold appearance, or germination capacity;
   determining by the processor of the post-harvest monitoring system according to the processor-executable instructions stored in the memory, a total safe storage time for the stored commodity based on the respective portion safe storage times for the plurality of portions of the stored commodity; and
   providing the total safe storage time as a display element of the user interface screen.

3. The post-harvest monitoring system of claim 2, wherein determining the portion safe storage time is additionally based on intergranular air movements created by temperature gradients.

4. The post-harvest monitoring system of claim 2, wherein the processor-executable instructions stored in the memory further cause the processor to determine an optimal aeration process for the stored commodity based on a model that incorporates effects of an aeration process and couples modeled temperature and moisture to external weather conditions at a geographic site for the storage facility.

5. The post-harvest monitoring system of claim 4, wherein the processor-executable instructions stored in the memory further cause the processor to determine a date and time to initiate the optimal aeration process in the storage facility and displays said date and time as additional user interface elements of the user interface screen.

6. The post-harvest monitoring system of claim 5, wherein the processor-executable instructions stored in the memory further cause the processor to control an aeration fan according to the optimal aeration process.

7. The post-harvest monitoring system of claim 1, wherein the processor-executable instructions stored in the memory further cause the processor to analyze the time-course data received at the post-harvest monitoring system from the sensors according to one or more detection models; display as elements in the user interface screen a notifications panel that includes a notification message when an event related to the stored commodity and/or the storage facility is detected through such analysis; and to automatically add an annotation to the time- course data, said annotation concerning the detected event.

8. The post-harvest monitoring system of claim 7, wherein the one or more detection models comprise statistical models or analytical equations with parameter fitting using optimization algorithms.

9. The post-harvest monitoring system of claim 7, wherein the time-course data includes $CO_2$ values.

10. The post-harvest monitoring system of claim 9, wherein the $CO_2$ values are decomposed to extract stored commodity condition and insect presence.

11. The post-harvest monitoring system of claim 1, wherein the processor-executable instructions stored in the memory further cause the processor to determine, based on detected levels of temperature, moisture content, and/or $CO_2$ concentrations within the storage facility, that a coring operation should be performed on the stored commodity; determine an amount of the commodity to be removed based on fill level data provided by a fill level sensor in the storage facility; and sort and display as a user interface element of the user interface screen time-course data of the fill level sensor in real-time.

12. The post-harvest monitoring system of claim 1, wherein the processor-executable instructions stored in the memory further cause the processor to analyze the time-course data according to one or more models based on storage facility dimensions, commodity condition, aeration fan characteristics, and weather conditions to produce a prediction of a commodity spoilage process; determine, based on the predicted commodity spoilage process, an aeration plan for spoilage process remediation; and automatically activate one or more aeration fans according to the aeration plan.

13. The post-harvest monitoring system of claim 1, wherein the aeration plan is determined in order to meet a greenhouse gas emission target related to expended energy.

14. The post-harvest monitoring system of claim 1, wherein the stored commodity quality metrics predictions and/or stored commodity business metrics predictions include some or all of infestation level, visible mold, dry matter loss, germination capacity, gas concentration, and estimates of commodity value and profit margin under a variety of post-harvest monitoring system-recommended or user-specified scenarios regarding potential remediation or other management activities for the stored commodity.

15. The post-harvest monitoring system of claim 14, wherein the stored commodity quality metrics are directly measured using one or more of the sensors, calculated based on a current direct measurement of a related physical descriptor, or predicted for a future time point.

16. The post-harvest monitoring system of claim 15, wherein the business metrics are computed using current or predicted ones of the commodity quality metrics, operational cost information, external predictions of stored commodity pricing, and the post-harvest monitoring system-recommended or user-specified scenarios regarding potential remediation or other management activities concerning the stored commodity.

17. The post-harvest monitoring system of claim 16, wherein the numerical model includes a computational fluid dynamics (CFD) simulation incorporating a finite volume approach for discretizing constituent equations, the an air flow component, an oxygen concentration component, a dry matter loss component, a visible mold component, and a germination loss component.

* * * * *